United States Patent [19]

Terahara et al.

[11] 4,438,277
[45] Mar. 20, 1984

[54] HYDRONAPHTHALENE DERIVATIVES

[75] Inventors: Akira Terahara; Kiyoshi Hamano; Yoshio Tsujita; Minoru Tanaka, all of Hiromachi, Japan

[73] Assignee: Sankyo Company, Limited, Tokyo, Japan

[21] Appl. No.: 368,673

[22] Filed: Apr. 15, 1982

Related U.S. Application Data

[62] Division of Ser. No. 256,243, Apr. 21, 1981, Pat. No. 4,361,515.

[30] Foreign Application Priority Data

Apr. 22, 1980 [JP] Japan .................................. 55-53057

[51] Int. Cl.³ .................. C07C 69/738; C07C 69/734; C07C 69/03
[52] U.S. Cl. ...................................... 560/119; 560/256
[58] Field of Search ............................... 560/119, 256

[56] References Cited

U.S. PATENT DOCUMENTS

| | | | |
|---|---|---|---|
| 4,137,322 | 1/1979 | Endo | 560/119 |
| 4,319,039 | 3/1982 | Albers-Schonberg | 560/119 |
| 4,346,227 | 8/1982 | Terahara | 560/119 |
| 4,376,863 | 3/1983 | Lam | 560/119 |

Primary Examiner—Michael L. Shippen
Attorney, Agent, or Firm—Frishauf, Holtz, Goodman & Woodward

[57] ABSTRACT

Compounds of formula (I):

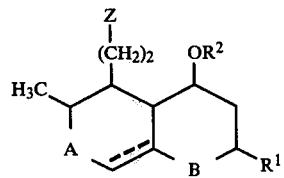

(I)

(in which:
Z represents a group of formula

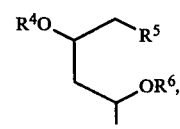

A represents a group of formula

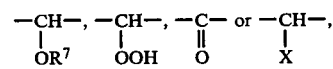

B represents a group of formula

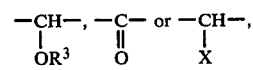

$R^1$ represents a hydrogen atom or a methyl group;
$R^2$, $R^3$, $R^4$ and $R^6$ are the same or different and each represents a hydrogen atom or an acyl group;
$R^5$ represents a carboxy group;
$R^7$ represents a hydrogen atom, an alkyl group or an acyl group;
X represents a halogen atom; and
the bond represents a double bond)
and salts and esters of the carboxy group represented by $R^5$ have useful anti-hypercholesteraemic activity and may be prepared from certain natural products obtainable by cultivation of microorganisms of the genera Penicillium or Monascus.

6 Claims, 3 Drawing Figures

HYDRONAPHTHALENE DERIVATIVES

This is a division of application Ser. No. 256,243 filed Apr. 21, 1981, now U.S. Pat. No. 4,361,515.

BACKGROUND TO THE INVENTION

The present invention relates to a series of novel compounds which have been found to inhibit cholesterol biosynthesis and which can thus be used in the treatment and prevention of disorders arising from high levels of cholesterol in the body. The invention also provides processes for preparing these compounds.

Hyperlipaemia, especially hypercholesteraemia, is known to be one of the main causes of cardiopathy, such as cardiac infarction or arteriosclerosis. As a result, considerable research has been carried out in an effort to discover capable of reducing lipid, and especially cholesterol, levels in the blood. A group of compounds of this type is disclosed in U.S. Pat. No. 3,983,140 and was isolated from the culture broth obtained by cultivating microorganisms of the genus Penicillium; this group of compounds is collectively designated ML-236. U.S. patent applications Ser. No. 121,515, filed Feb. 14, 1980, and No. 137,821, filed Apr. 4, 1980, which issued as U.S. Pat. No. 4,323,648 on Apr. 6, 1982, disclosed a structurally similar compound designated Monacolin K or MB-530B, and certain salts and esters of MB-530B are disclosed in U.S. patent application Ser. No. 172,231, filed July 25, 1980. MB-530B and its salts may be prepared by cultivating microorganisms of the genus Monascus, especially, but not exclusively, strains of *Monascus ruber*. Another compound of the MB-530 group, designated MB-530A, as well as other compounds relating to the ML-236 and MB-530 groups are disclosed in co-pending Application Ser. No. 247,875 filed Mar. 30, 1981 entitled "Inhibitors of Cholesterol Biosynthesis, their Preparation and Use" and Application Ser. No. 251,733 filed Apr. 7, 1981 entitled "Compounds which Inhibit Cholesterol Biosynthesis, and their Preparation" to A. Sato et al..

We have now discovered a series of compounds related to these prior compounds which also have valuable inhibitory activity against the biosynthesis of cholesterol.

BRIEF DESCRIPTION OF INVENTION

The compounds of the invention have the formula (I):

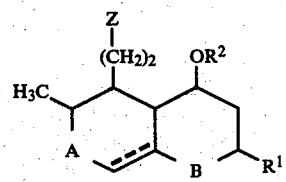

(in which:
Z represents a group of formula

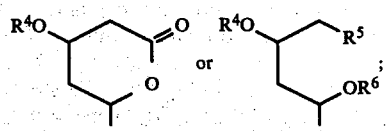

A represents a group of formula

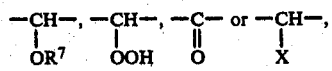

B represents a group of formula

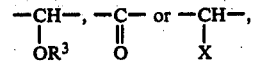

$R^1$ represents a hydrogen atom or a methyl group;
$R^2$, $R^3$, $R^4$ and $R^6$ are the same or different and each represents a hydrogen atom or an acyl group;
$R^5$ represents a carboxy group;
$R^7$ represents a hydrogen atom, an alkyl group or an acyl group;
X represents a halogen atom; and
the bond ≡≡≡ represents a single or double bond;
and salts and esters of the carboxyl group represented by $R^5$.

Also provided by the present invention are epoxides of formula (II), which are closely related to the above compounds of formula (I):

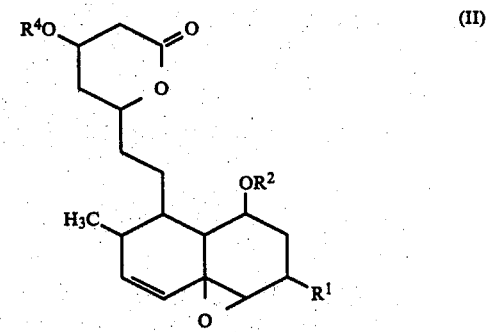

(in which $R^1$, $R^2$ and $R^4$ are as defined above).

DETAILED DESCRIPTION OF INVENTION

Figure 1:
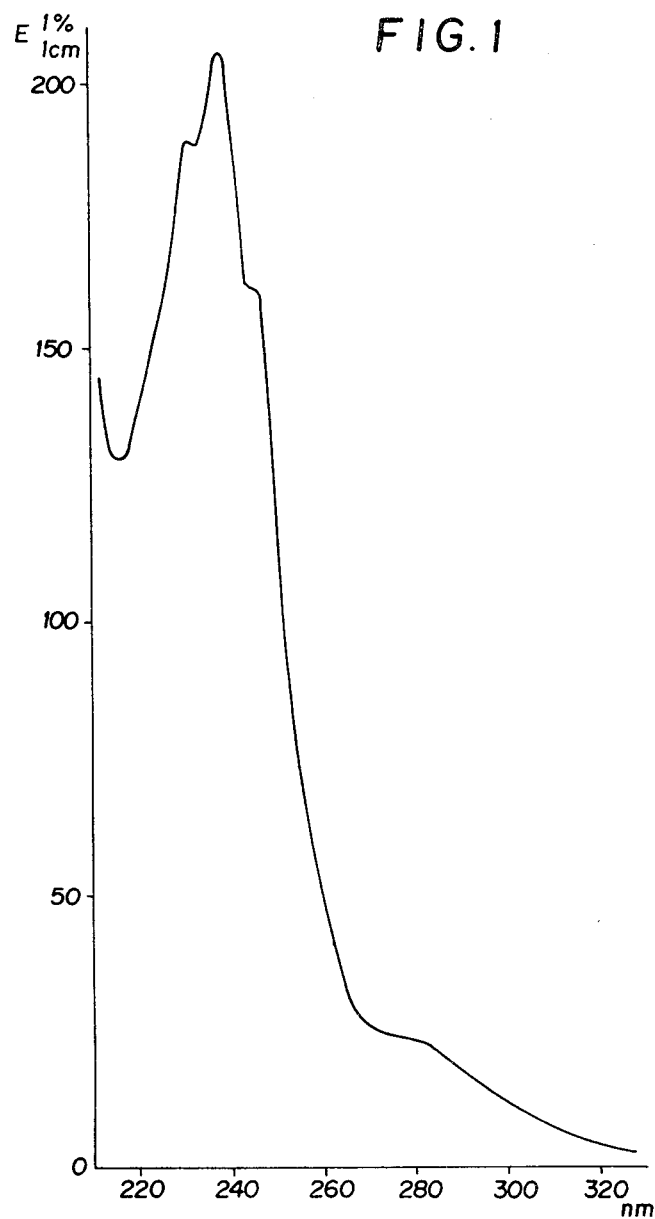

As the compounds of the invention are derivatives of the ML-236 and MB-530 group compounds, they are named as hydrogenated derivatives of ML-236A, ML-236B, MB-530A or MB-530B or of the corresponding carboxylic acids according to the following scheme:

Compounds of formula (A):

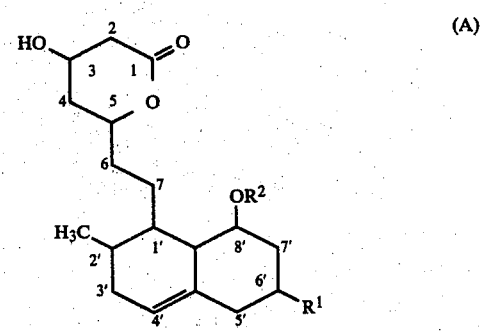

(i) in which $R^1$ and $R^2$ both represent hydrogen atoms is called dihydro-ML-236A (DH.ML-236A);

(ii) in which $R^1$ represents a hydrogen atom and $R^2$ represents an α-methylbutyryl group is called dihydro-ML-236B (DH.ML-236B);

(iii) in which $R^1$ represents a methyl group and $R^2$ represents a hydrogen atom is called dihydro-MB-530A (DH.MB-530A);

(iv) in which $R^1$ represents a methyl group and $R^2$ represents an α-methylbutyryl group is called dihydro-MB-530B (DH.MB-530B);

Compounds of formula (B):

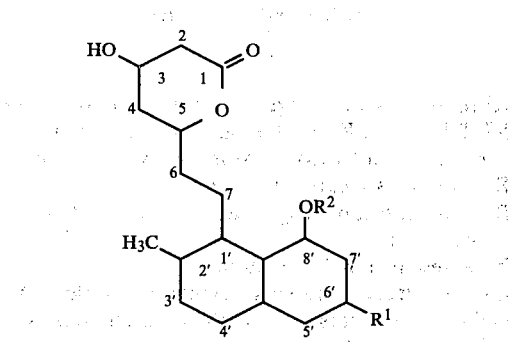

(i) in which $R^1$ and $R^2$ both represent hydrogen atoms is called tetrahydro-ML-236A (TH.ML-236A);

(ii) in which $R^1$ represents a hydrogen atom and $R^2$ represents an α-methylbutyryl group is called tetrahydro-ML-236B (TH.ML-236B);

(iii) in which $R^1$ represents a methyl group and $R^2$ represents a hydrogen atom is called tetrahydro-MB-530A (TH.MB-530A);

(iv) in which $R^1$ represents a methyl group and $R^2$ represents an α-methylbutyryl group is called tetrahydro-MB-530B (TH.MB-530B);

COmpounds of formula (C):

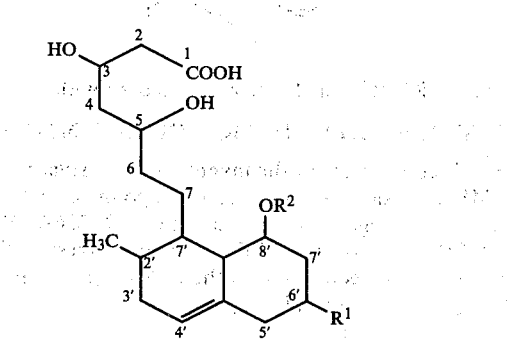

(i) in which $R^1$ and $R^2$ both represent hydrogen atoms is called dihydro-ML-236A carboxylic acid (DH.ML-236A carboxylic acid);

(ii) in which $R^1$ represents a hydrogen atom and $R^2$ represents an α-methylbutyryl group is called dihydro-ML-236B carboxylic acid (DH.ML-236B carboxylic acid);

(iii) in which $R^1$ represents a methyl group and $R^2$ represents a hydrogen atom is called dihydro-MB-530A carboxylic acid (DH.MB-530A carboxylic acid);

(iv) in which $R^1$ represents a methyl group and $R^2$ represents an α-methylbutyryl group is called dihydro-MB-530B carboxylic acid (DH.MB-530B carboxylic acid); and Compounds of formula (D):

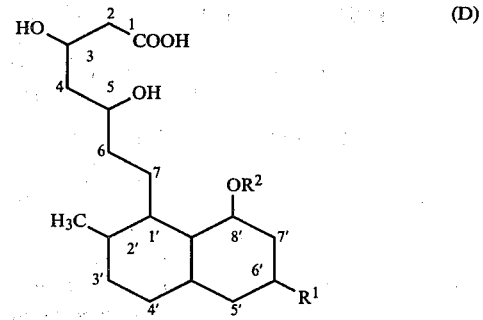

(i) in which $R^1$ and $R^2$ both represent hydrogen atoms is called tetrahydro-ML-236A carboxylic acid (TH.ML-236A carboxylic acid);

(ii) in which $R^1$ represents a hydrogen atom and $R^2$ represents an α-methylbutyryl group is called tetrahydro-ML-236B carboxylic acid (TH.ML-236B carboxylic acid);

(iii) in which $R^1$ represents a methyl group and $R^2$ represents a hydrogen atom is called tetrahydro-MB-530A carboxylic acid (TH.MB-530A carboxylic acid);

(iv) in which $R^1$ represents a methyl group and $R^2$ represents an α-methylbutyryl group is called tetrahydro-MB-530B carboxylic acid (TH.MB-530B carboxylic acid).

Acylated derivatives of the above compounds are then named in the usual way using the above structures as the parent compound. Expoxides of formula (II) are simply named as epoxides of ML-236A, ML-236B, MB-530A or MB-530B or of their acylated derivatives.

In the compounds of formula (I) and (II), $R^2$, $R^3$, $R^4$ and $R^6$ may represent hydrogen atoms or acyl groups and $R^7$ may represent a hydrogen atom, an alkyl group or as acyl group. Where these groups represent an acyl group, it may be an organic acyl group (for example an aliphatic acyl group, an aromatic acyl group, an araliphatic acyl group, an alicyclic acyl group, a heterocyclic acyl group, a heterocyclic-substituted aliphatic acyl group, an aliphatic sulphonyl group, an aromatic sulphonyl group, an aliphatic phosphoryl group, an aromatic phosphoryl group or an araliphatic phosphoryl group) or an inorganic acyl group (for example an acyl group derived from phosphoric acid, sulphuric acid or nitric acid).

Where the acyl group is an aliphatic acyl group, this may be saturated or unsaturated and examples include: straight or branched chain $C_2$–$C_{20}$ alkanoyl groups (e.g. the acetyl, propionyl, butyryl, isobutyryl, valeryl, isovaleryl, pivaloyl, hexanoyl, 2-methylvaleryl, heptanoyl, isoheptanoyl, octanoyl, isooctanoyl, 2-methyloctanoyl, nonanoyl, isononanoyl, decanoyl, undecanoyl, dodecanoyl, tridecanoyl, tetradecanoyl, pentadecanoyl, palmitoyl, stearoyl, isostearoyl, nonadecanoyl and eicosanoyl groups); $C_3$–$C_{20}$ alkenoyl groups (e.g. the acryloyl, crotonoyl, 3-butenoyl, methacryloyl, 3-methyl-2-butenoyl, 2-pentenoyl, 4-pentenoyl, tigloyl, angeloyl, 2-hexenoyl, 2-heptenoyl, hepta-2,4-dienoyl, 2-octenoyl, 2-nonenoyl, 2-decenoyl, 2-undecenoyl, linolenoyl, oleoyl, linoleoyl and arachidonoyl groups); and $C_3$–$C_{20}$ alkynoyl groups (e.g. the propioloyl, 2-butynoyl, 3-butynoyl, 2-pentynoyl, 2-hexynoyl, 2-heptynoyl, 2-octynoyl, 2-nonynoyl and 2-decynoyl groups). These acyl groups may be unsubstituted or may have one or more substituents, for example: halogen atoms, such as chlorine or bromine; the trifluoromethyl group; the nitro group; the carboxy group; alkoxycarbonyl groups, such as methoxycarbonyl or ethoxycarbonyl; aralkoxycarbonyl groups, such as benzyloxycarbonyl; the cyano group; the amino group; alkanoylamino groups, such as acetylamino; alkylamino groups, such as methylamino, dimethylamino or ethylamino; aralkylamino groups, such as benzylamino; the hydroxy group; alkanoyloxy groups, such as acetoxy or pivaloyloxy; alkoxy groups, such as methoxy or ethoxy; the sulphhydryl group; alkylthio groups, such as methylthio or ethylthio; and acylthio groups, such as acetylthio or benzylthio.

Where the acyl group represented by $R^2$-$R^4$, $R^6$ or $R^7$ is an aromatic acyl group, the aromatic ring may be a single ring (e.g. a benzene ring) or a fused ring, for example a naphthalene ring, an anthracene ring or an indan ring. This ring may optionally have one or more substituents, for example alkyl groups, alkoxy groups, halogen atoms, trifluoromethyl groups, nitro groups, cyano groups, amino groups or hydroxy groups; where there are two or more substituents, these may be the same or different. Specific examples of such aromatic acyl groups include the benzoyl, o-toluoyl, m-toluoyl, p-toluoyl, 2,4-dimethylbenzoyl, 3,4-dimethylbenzoyl, 2-ethylbenzoyl, 3-ethylbenzoyl, 4-ethylbenzoyl, 2-propylbenzoyl, 3-propylbenzoyl, 4-propylbenzoyl, 4-butylbenzoyl, o-anisoyl, m-anisoyl, p-anisoyl, 2,4-dimethoxybenzoyl, 2-ethoxybenzoyl, 3-ethoxybenzoyl, 4-ethoxybenzoyl, 2-propoxybenzoyl, 3-propoxybenzoyl, 4-propoxybenzoyl, 2-butoxybenzoyl, 3-butoxybenzoyl, 4-butoxybenzoyl, piperonyloyl, 2-chlorobenzoyl, 3-chlorobenzoyl, 4-chlorobenzoyl, 2,3-dichlorobenzoyl, 3,4-dichlorobenzoyl, 2,4-dichlorobenzoyl, 2-bromobenzoyl, 3-bromobenzoyl, 4-bromobenzoyl, 2-fluorobenzoyl, 3-fluorobenzoyl, 4-fluorobenzoyl, 2-trifluoromethylbenzoyl, 3-trifluoromethylbenzoyl, 4-trifluoromethylbenzoyl, 2-nitrobenzoyl, 3-nitrobenzoyl, 4-nitrobenzoyl, 2,4-dinitrobenzoyl, 3,5-dinitrobenzoyl, salicyloyl, 3-hydroxybenzoyl, 4-hydroxybenzoyl, 2-acetoxybenzoyl, 3-acetoxybenzoyl, 4-acetoxybenzoyl, anthraniloyl, 2-acetamidobenzoyl, 4-acetamidobenzoyl, vanilloyl, veratroyl, protocatechuoyl, galloyl, 1-naphthoyl, 2-naphthoyl, 2-anthranoyl, 4-indanecarbonyl, 5-indanecarbonyl and 4-indenecarbonyl groups.

Where the acyl group represented by $R^2$-$R^4$, $R^6$ or $R^7$ is an araliphatic acyl group, the aromatic ring in this araliphatic acyl group may be a single ring or a fused ring, as exemplified above for the aromatic acyl group, whilst the aliphatic moiety may be saturated or unsaturated. The aromatic ring may optionally have one or more substituents, as exemplified above for the aromatic acyl groups. Examples of such araliphatic acyl groups include the phenylacetyl, 2-methylphenylacetyl, 3-methylphenylacetyl, 4-methylphenylacetyl, 2-ethylphenylacetyl, 2-methoxyphenylacetyl, 3-methoxyphenylacetyl, 4-methoxyphenylacetyl, 2-ethoxyphenylacetyl, 3-ethoxyphenylacetyl, 4-ethoxyphenylacetyl, 2-propoxyphenylacetyl, 3-propoxyphenylacetyl, 4-propoxyphenylacetyl, 2,4-dimethoxyphenylacetyl, 3,4-methylenedioxyphenylacetyl, 2-hydroxyphenylacetyl, 3-hydroxyphenylacetyl, 4-hydroxyphenylacetyl, 2-chlorophenylacetyl, 3-chlorophenylacetyl, 4-chlorophenylacetyl, 2,3-dichlorophenylacetyl, 2,4-dichlorophenylacetyl, 3,5-dichlorophenylacetyl, 2-bromophenylacetyl, 3-bromophenylacetyl, 4-bromophenylacetyl, 2-nitrophenylacetyl, 3-nitrophenylacetyl, 4-nitrophenylacetyl, 4-aminophenylacetyl, 2-phenylpropionyl, 3-(2-methylphenyl)propionyl, 3-(3-methylphenyl)propionyl, 3-(4-methylphenyl)propionyl, 3-(2-methoxyphenyl)propionyl, 3-(3-methoxyphenyl)propionyl, 3-(4-methoxyphenyl)propionyl, 3-(3,4-methylenedioxyphenyl)propionyl, 3-(2-chlorophenyl)propionyl, 3-(3-chlorophenyl)propionyl, 3-(4-chlorophenyl)propionyl, phenoxyacetyl, cinnamoyl, o-methylcinnamoyl, m-methylcinnamoyl, p-methylcinnamoyl, o-methoxycinnamoyl, m-methoxycinnamoyl, p-methoxycinnamoyl, o-hydroxycinnamoyl, m-hydroxycinnamoyl, p-hydroxycinnamoyl, o-chlorocinnamoyl, m-chlorocinnamoyl, p-chlorocinnamoyl, o-bromocinnamoyl, m-bromocinnamoyl and p-bromocinnamoyl groups.

Where the acyl group represented by $R^2$-$R^4$, $R^6$ or $R^7$ is an alicyclic acyl group, the alicyclic ring may be saturated or unsaturated and preferably has from 3 to 7 carbon atoms. Examples of such alicyclic acyl groups include the cyclopropanecarbonyl, cyclobutanecarbonyl, cyclobut-1-enecarbonyl, cyclobut-2-enecarbonyl, cyclopentanecarbonyl, cyclopent-1-enecarbonyl, cyclopent-2-enecarbonyl, cyclopenta-1,3-dienecarbonyl, cyclopenta-2,4-dienecarbonyl, cyclohexanecarbonyl, cyclohex-1-enecarbonyl, cyclohex-2-enecarbonyl, cyclohex-3-enecarbonyl, cyclohexa-1,3-dienecarbonyl, cyclohexa-2,4-dienecarbonyl, cycloheptanecarbonyl, cyclohept-1-enecarbonyl, cyclohept-2-enecarbonyl, cyclohept-3-enecarbonyl, cyclohepta-1,3-dienecarbonyl, cyclohepta-2,4-dienecarbonyl, cyclohepta-2,5-dienecarbonyl, cyclohepta-1,4-dienecarbonyl, cyclohepta-1,5-dienecarbonyl, cyclohepta-1,3,5-trienecarbonyl, cyclohepta-2,4,6-trienecarbonyl and adamantanecarbonyl groups. These rings may optionally have one or more substituents, as exemplified above in respect of the aromatic acyl groups and such substituents may form one or more rings fused to the above-mentioned alicyclic ring system.

Where the acyl group represented by $R^2$-$R^4$, $R^6$ or $R^7$ is a heterocyclic acyl group, the heterocyclic ring preferably has 5 or 6 ring atoms, one or more of which is a hetero atom, for example a nitrogen atom, an oxygen atom, a sulphur atom or a selenium atom. This heterocyclic ring may optionally be fused with a carbocyclic ring or with another heterocyclic ring (which may be the same as or different from the first-mentioned heterocyclic ring) to form a fused heterocyclic ring system. The heterocyclic acyl group may have one or more substituents, as exemplified above in respect of the aromatic acyl groups. Specific examples of such heterocyclic acyl groups include the 2-thenoyl, 3-thenoyl, 5-methylthen-2-oyl, 5-chlorothen-2-oyl, 4,5-dimethylthen-3-oyl, 2-furoyl, 3-furoyl, 5-methylfur-2-oyl, 5-chlorofur-2-oyl, pyridine-2-carbonyl, 3-methylpyridine-2-carbonyl, 4-methylpyridine-2-carbonyl, 5-methylpyridine-2-carbonyl, 6-methylpyridine-2-carbonyl, nicotinoyl, isonicotinoyl, isoxazole-3-carbonyl, isoxazole-4-carbonyl, oxazole-2-carbonyl, oxazole-4-carbonyl, 4-acetylaminothiazole-2-carbonyl, 1,3,4-thiadiazole-2-carbonyl, 5-methyl-1,3,4-thiadiazole-2-carbonyl, 1,2,3-triazole-1-carbonyl, 1,2,3,4-tetrazole-1-carbonyl, piperidinecarbonyl, 4-methyl-1-piperazinecarbonyl, 1-pyrrolidinecarbonyl, benzofuran-2-carbonyl and benzothiophene-2-carbonyl groups.

Where the acyl group represented by $R^2$-$R^4$, $R^6$ or $R^7$ is a heterocyclic-substituted aliphatic acyl group, the heterocyclic group may be as described above for the heterocyclic acyl groups and the aliphatic moiety may be saturated or unsaturated and may be as described above for aliphatic acyl groups. Examples of such heterocyclic-substituted aliphatic acyl groups include the 2-thienylacetyl, (5-methylthiophene-2-yl)acetyl, (5-chlorothiophene-2-yl)acetyl, 3-thienylacetyl, 2-furylacetyl, 3-furylacetyl, 2-pyridylacetyl, 3-pyridylacetyl, 4-pyridylacetyl, 2-furylacryloyl, 3-furylacryloyl, 2-thienylacryloyl, 3-thienylacryloyl, piperidinoacetyl and 4-methylpiperidinoacetyl, 2-amino-3-(indol-2-yl)propionyl and 2-amino-3-(indol-3-yl)propionyl groups.

Where the acyl group represented by $R^2$-$R^4$, $R^6$ or $R^7$ is a sulphonyl group, this may be an aliphatic sulphonyl group (for example a methanesulphonyl or ethanesulphonyl group) or an aromatic sulphonyl group (e.g. a benzenesulphonyl or toluenesulphonyl group).

Where the acyl group represented by $R^2$-$R^4$, $R^6$ or $R^7$ is a phosphoryl group, this may be an aliphatic phosphoryl group (e.g. a dimethylphosphoryl or diethylphosphoryl group), an aromatic phosphoryl group (e.g. a ditolylphosphoryl group) or an araliphatic phosphoryl group (e.g. a dibenzylphosphoryl, p-methylbenzylphosphoryl, p-bromobenzylphosphoryl or p-methoxybenzylphosphoryl group).

Where $R^7$ represents an alkyl group, this may be a straight or branched chain $C_1$-$C_6$ alkyl group, such as a methyl, ethyl, propyl, isopropyl, butyl, isobutyl, sec-butyl, t-butyl, pentyl, 2-methylbutyl, 1-methylbutyl, 1,1-dimethylpropyl, 1,2-dimethylpropyl, 3-methylbutyl, neopentyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,3-dimethylbutyl, 1,1,2-trimethylbutyl, 1,2,2-trimethylpropyl, 1-ethylbutyl, 2-ethylbutyl, 3-ethylbutyl, 1-methyl-1-ethylpropyl, 1-ethyl-2-methylpropyl or 2,2-dimethylbutyl group.

In the compounds of formula (I), $R^5$ represents a carboxy group. However, the present invention also provides salts and esters of these compounds, i.e. compounds of formula (I) in which $R^5$ represents a group of formula -COO(R')$_r$, in which R' represents the alcoholic moiety of an ester or the cationic moiety of a salt and r represents the reciprocal of the valency of R'.

In the salts of compounds of formula (I), where R' represents the cationic moiety of a salt, it may be a metal atom, for example an alkali metal atom (e.g. sodium or potassium), an alkaline earth metal atom (e.g. calcium, magnesium or barium), a transition metal atom (e.g. iron, nickel or cobalt) or other metal atoms (e.g. aluminium, zinc or copper), in this case, r will be the reciprocal of the well-known valency of these metals, the valency being, in the examples given, normally from 1 to 3. Alternatively, it may be an ammonium group or a substituted ammonium group (preferably an alkyl-substituted ammonium group), such as methylammonium, ethylammonium, isopropylammonium, dimethylammonium, diethylammonium, trimethylammonium, triethylammonium, tetramethylammonium or dicyclohexylammonium, in this case, r will be 1. Another cationic moiety which may be represented by R' is the salt-forming group derived from a basic amino acid, such as lysine, arginine or ornithine.

Alternatively, R' may represent the alcoholic moiety of an ester, in which case the value of r will depend upon the nature of the hydroxy-compound from which R' is derived; for example, if the ester is an ester of a monoalcohol, r would be 1; in the case of glycols, r would be ½; and, in the case of glycerol, r would be ⅓. Where R' represents a monovalent group, this is preferably an unsubstituted or substituted alkyl group, an unsubstituted or substituted aralkyl group or an unsubstituted or substituted phenacyl group.

Examples of alkyl groups which may be represented by R' include straight and branched chain alkyl groups, preferably having from 1 to 8 carbon atoms, for example the methyl, ethyl, propyl, isopropyl, butyl, isobutyl, sec-butyl, t-butyl, pentyl, sec-pentyl, t-pentyl, isopentyl, neopentyl, hexyl, heptyl, 2-methylhexyl and octyl groups.

Examples of aralkyl groups which may be represented by R' include the benzyl group and the benzhydryl group, both of which may be unsubstituted or have one or more substituents in the benzene ring. Examples of such substituents include: $C_1$-$C_4$ alkyl groups (methyl, ethyl, propyl, isopropyl, butyl, isobutyl, sec-butyl or t-butyl), $C_1$-$C_4$ alkoxy groups (methoxy, ethoxy, propoxy, isopropoxy, butoxy, isobutoxy, sec-butoxy or t-butoxy), halogen atoms (e.g. chlorine, bromine or fluorine) or the trifluoromethyl group. Where there are two or more substituents, these may be the same or different. Examples of such aralkyl groups include the benzyl, 2-methylbenzyl, 3-methylbenzyl, 4-methylbenzyl, 2-ethylbenzyl, 3-ethylbenzyl, 4-ethylbenzyl, 2-propylbenzyl, 3-propylbenzyl, 4-propylbenzyl, 2-butylbenzyl, 3-butylbenzyl, 4-butylbenzyl, 2-methoxybenzyl, 3-methoxybenzyl, 4-methoxybenzyl, 2-propoxybenzyl, 3-propoxybenzyl, 4-propoxybenzyl, 4-butoxybenzyl, 2-chlorobenzyl, 3-chlorobenzyl, 4-chlorobenzyl, 2-bromobenzyl, 3-bromobenzyl, 4-bromobenzyl, 2-fluorobenzyl, 3-fluorobenzyl, 4-fluorobenzyl, 2-trifluoromethylbenzyl, 3-trifluoromethylbenzyl, 4-trifluoromethylbenzyl and benzhydryl groups.

Where R' represents a phenacyl group, this may be unsubstituted or may have one or more substituents in the benzene ring. Examples of such substituents include: $C_1$-$C_4$ alkyl groups, $C_1$-$C_4$ alkoxy groups, halogen atoms and the trifluoromethyl group; specific examples of these substituent groups are given above. Preferred examples of such phenacyl groups include the phenacyl, 2-methylphenacyl, 3-methylphenacyl, 4-methylphenacyl, 2-ethylphenacyl, 3-ethylphenacyl, 4-ethylphenacyl, 2-propylphenacyl, 3-propylphenacyl, 4-propylphenacyl, 2-butylphenacyl, 3-butylphenacyl, 4-butylphenacyl, 2-methoxyphenacyl, 3-methoxyphenacyl, 4-methoxyphenacyl, 2-ethoxyphenacyl, 3-ethoxyphenacyl, 4-ethoxyphenacyl, 2-propoxyphenacyl, 3-propoxyphenacyl, 4-propoxyphenacyl, 2-butoxyphenacyl, 3-butoxyphenacyl, 4-butoxyphenacyl, 2-chlorophenacyl, 3-chlorophenacyl, 4-chlorophenacyl, 2-bromophenacyl, 3-bromophenacyl, 4-bromophenacyl, 2-fluorophenacyl, 3-fluorophenacyl, 4-fluorophenacyl, 2-trifluoromethylphenacyl, 3-trifluoromethylphenacyl and 4-trifluoromethylphenacyl groups.

Where R' represents a bivalent alcoholic moiety, it is preferably a $C_2$-$C_6$ alkylene or alkylidene group, for example an ethylene, ethylidene, propylene, propylidene, trimethylene, tetramethylene, butylidene, pentamethylene or pentylidene group, as well as such groups having one or more substituents, e.g. hydroxy groups, halogen atoms or trifluoromethyl groups.

Where R' represents a trivalent alcoholic moiety, it is preferably a saturated aliphatic hydrocarbon group having from 2 to 6 carbon atoms and optionally one or more substituents, e.g. hydroxy groups, halogen atoms or trifluoromethyl groups.

X, which represents a halogen atom, is preferably a chlorine or bromine atom.

Within the compounds of formula (I), there are included lactones of formula (Ia):

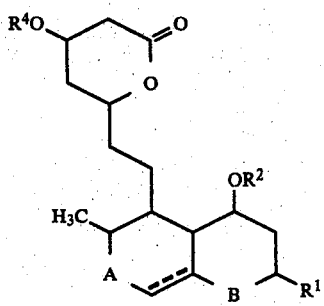

(Ia)

(in which A, B, $R^1$, $R^2$ and $R^4$ are as defined above) and their corresponding carboxylic acids of formula (Ib):

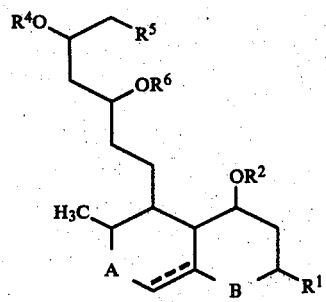

(Ib)

(in which A, B, $R^1$, $R^2$, $R^4$, $R^5$ and $R^6$ are as defined above) and salts and esters of the carboxy group represented by $R^5$ in said carboxylic acid of formula (Ib).

Of the compounds of formula (I), (Ia) and (Ib), preferred compounds are those in which:

$R^2$, $R^3$, $R^4$ and $R^6$ are the same or different and each represents a straight or branched chain $C_2$-$C_{20}$ alkanoyl group, a straight or branched chain $C_3$-$C_{20}$ alkenoyl group or a benzoyl group, and $R^7$ represents a hydrogen atom, a straight or branched chain $C_1$-$C_6$ alkyl group, a straight or branched chain $C_2$-$C_{20}$ alkanoyl group, a straight or branched chain $C_3$-$C_{20}$ alkenoyl group or a benzoyl group.

In the case of salts and esters of the compounds of formula (I) and (Ib), we prefer the metal salts, the ammonium salts, the alkyl-substituted ammonium salts, the basic amino acid salts, straight or branched chain $C_1$-$C_4$ alkyl esters and the benzyl esters. Most preferably, the salts are the alkali metal salts and the esters are the straight or branched chain $C_1$-$C_4$ alkyl esters.

Amongst the compounds of the invention, a preferred class of compounds is represented by the formula (Ic):

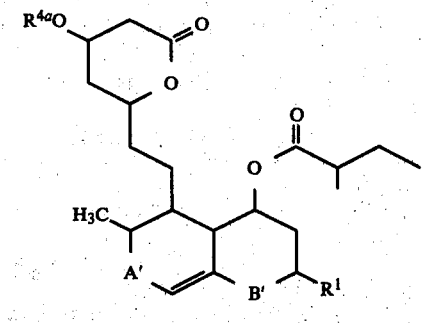

(Ic)

in which:

$R^1$ represents a hydrogen atom or a methyl group, $R^{4a}$ represents a hydrogen atom or a straight or branched chain $C_1$-$C_6$ alkanoyl group;

$A^1$ represents a group of formula

(in which $R^8$ represents a hydrogen atom, a straight or branched chain $C_1$-$C_4$ alkyl group or a straight or branched chain $C_2$-$C_6$ alkanoyl group), a group of formula

(in which X represents a halogen atom) or a group of formula

$B^1$ represents a group of formula

(in which $R^9$ represents a hydrogen atom or a straight or branched chain $C_2$-$C_6$ alkanoyl group), a group of formula

(in which X represents a halogen atom) or a group of formula

A further preferred class of compounds of the invention are those compounds of formula (Id):

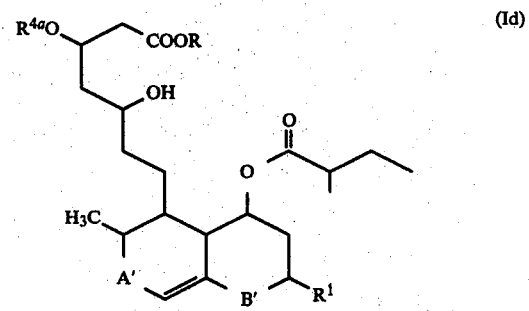

(Id)

in which:

R represents an alkali metal or a straight or branched chain $C_1$-$C_4$ alkyl group; and $R^1$, $R^{4a}$, A and B are as defined above.

In the case of the epoxides of formula (II), particularly preferred compounds are those in which $R^2$ represents an α-methylbutyryl group and R⁴ represents a hydrogen atom.

Specific examples of compounds of the invention are given in the following list.

1. 3',5'-Dihydroxy-(DH.ML-236A)
2. 3',5'-Dihydroxy-(DH.MB-530A)
3. 3-(O-Acetyl)-3',5'-dihydroxy-(DH.ML-236A)
4. 3-(O-Propionyl)-3',5'-dihydroxy-(DH.ML-236A)
5. 3-(O-Butyryl)-3',5'-dihydroxy-(DH.ML-236A)
6. 3-(O-Valeryl)-3',5'-dihydroxy-(DH.ML-236A)
7. 3-(O-Isovaleryl)-3',5'-dihydroxy-(DH.ML-236A)
8. 3-(O-Acryloyl)-3',5'-dihydroxy-(DH.ML-236A)
9. 3-(O-Palmitoyl)-3',5'-dihydroxy-(DH.ML-236A)
10. 3-(O-Stearoyl)-3',5'-dihydroxy-(DH.ML-236A)
11. 3-(O-Linolenoyl)-3',5'-dihydroxy-(DH.ML-236A)
12. 3-(O-Benzoyl)-3',5'-dihydroxy-(DH.ML-236A)
13. 3-(O-p-Toluoyl)-3',5'-dihydroxy-(DH.ML-236A)
14. 3-(O-2-Chlorobenzoyl)-3',5'-dihydroxy-(DH.ML-236A)
15. 3-(O-2-Bromobenzoyl)-3',5'-dihydroxy-(DH.ML-236A)
16. 3-(O-Salicyloyl)-3',5'-dihydroxy-(DH.ML-236A)
17. 3-(O-Phenylacetyl)-3',5'-dihydroxy-(DH.ML-236A)
18. 3-(O-Cinnamoyl)-3',5'-dihydroxy-(DH.ML-236A)
19. 3-(O-Cyclohexanecarbonyl)-3',5'-dihydroxy-(DH.ML-236A)
20. 3-(O-2-Thenoyl)-3',5'-dihydroxy-(DH.ML-236A)
21. 3-(O-2-Furoyl)-3',5'-dihydroxy-(DH.ML-236A)
22. 3-(O-2-Thienylacetyl)-3',5'-dihydroxy-(DH.ML-236A)
23. 3-(O-Acetyl)-3',5'-dihydroxy-(DH.MB-530A)
24. 3-(O-Propionyl)-3',5'-dihydroxy-(DH.MB-530A)
25. 3-(O-Butyryl)-3',5'-dihydroxy-(DH.MB-530A)
26. 3-(O-Valeryl)-3',5'-dihydroxy-(DH.MB-530A)
27. 3-(O-Isovaleryl)-3',5'-dihydroxy-(DH.MB-530A)
28. 3-(O-Acryloyl)-3',5'-dihydroxy-(DH.MB-530A)
29. 3-(O-Palmitoyl)-3',5'-dihydroxy-(DH.MB-530A)
30. 3-(O-Stearoyl)-3',5'-dihydroxy-(DH.MB-530A)
31. 3-(O-Linolenoyl)-3',5'-dihydroxy-(DH.MB-530A)
32. 3-(O-Benzoyl)-3',5'-dihydroxy-(DH.MB-530A)
33. 3-(O-p-Toluoyl)-3',5'-dihydroxy-(DH.MB-530A)
34. 3-(O-2-Chlorobenzoyl)-3',5'-dihydroxy-(DH.MB-530A)
35. 3-(O-2-Bromobenzoyl)-3',5'-dihydroxy-(DH.MB-530A)
36. 3-(O-Salicyloyl)-3',5'-dihydroxy-(DH.MB-530A)
37. 3-(O-Phenylacetyl)-3',5'-dihydroxy-(DH.MB-530A)
38. 3-(O-Cinnamoyl)-3',5'-dihydroxy-(DH.MB-530A)
39. 3-(O-Cyclohexanecarbonyl)-3',5'-dihydroxy-(DH.MB-530A)
40. 3-(O-2-Thenoyl)-3',5'-dihydroxy-(DH.MB-530A)
41. 3-(O-2-Furoyl)-3',5'-dihydroxy-(DH.MB-530A)
42. 3-(O-2-Thienylacetyl)-3',5'-dihydroxy-(DH.MB-530A)
43. 8'-(O-Acetyl)-3',5'-dihydroxy-(DH.ML-236A)
44. 8'-(O-Butyryl)-3',5'-dihydroxy-(DH.ML-236A)
45. 3',5'-Dihydroxy-(DH.ML-236B)
46. 8'-(O-Linolenoyl)-3',5'-dihydroxy-(DH.ML-236A)
47. 8'-(O-Benzoyl)-3',5'-dihydroxy-(DH.ML-236A)
48. 8'-(O-Phenylacetyl)-3',5'-dihydroxy-(DH.ML-236A)
49. 8'-(O-2-Thenoyl)-3',5'-dihydroxy-(DH.ML-236A)
50. 8'-(O-Acetyl)-3',5'-dihydroxy-(DH.MB-530A)
51. 8'-(O-Butyryl)-3',5'-dihydroxy-(DH.MB-530A)
52. 3',5'-Dihydroxy-(DH.MB-530B)
53. 8'-(O-Linolenoyl)-3',5'-dihydroxy-(DH.MB-530A)
54. 8'-(O-Benzoyl)-3',5'-dihydroxy-(DH.MB-530A)
55. 8'-(O-Phenylacetyl)-3',5'-dihydroxy-(DH.MB-530A)
56. 8'-(O-2-Thenoyl)-3',5'-dihydroxy-(DH.MB-530A)
57. 3,8'-Di(O-acetyl)-3',5'-dihydroxy-(DH.ML-236A)
58. 3,8'-Di(O-butyryl)-3',5'-dihydroxy-(DH.ML-236A)
59. 3-(O-2-Methylbutyryl)-3',5'-dihydroxy-(DH.ML-236B)
60. 3,8'-Di(O-stearoyl)-3',5'-dihydroxy-(DH.ML-236A)
61. 3,8'-Di(O-linolenoyl)-3',5'-dihydroxy-(DH.ML-236A)
62. 3,8'-Di(O-benzoyl)-3',5'-dihydroxy-(DH.ML-236A)
63. 3,8'-Di(O-phenylacetyl)-3',5'-dihydroxy-(DH.ML-236A)
64. 3,8'-Di(O-2-thienylacetyl)-3',5'-dihydroxy-(DH.ML-236A)
65. 3,8'-Di(O-2-thenoyl)-3',5'-dihydroxy-(DH.ML-236A)
66. 3-(O-Acetyl)-3',5'-dihydroxy-(DH.ML-236B)
67. 3-(O-Propionyl)-3',5'-dihydroxy-(DH.ML-236B)
68. 3-(O-Butyryl)-3',5'-dihydroxy-(DH.ML-236B)
69. 3-(O-Stearoyl)-3',5'-dihydroxy-(DH.ML-236B)
70. 3-(O-Linolenoyl)-3',5'-dihydroxy-(DH.ML-236B)
71. 3-(O-Benzoyl)-3',5'-dihydroxy-(DH.ML-236B)
72. 3-(O-Salicyloyl)-3',5'-dihydroxy-(DH.ML-236B)
73. 3-(O-Phenylacetyl)-3',5'-dihydroxy-(DH.ML-236B)
74. 3-(O-Cinnamoyl)-3',5'-dihydroxy-(DH.ML-236B)
75. 3-(O-2-Thenoyl)-3',5'-dihydroxy-(DH.ML-236B)
76. 3-(O-2-Thienylacetyl)-3',5'-dihydroxy-(DH.ML-236B)
77. 3-(O-Acetyl)-8'-(O-butyryl)-3',5'-dihydroxy-(DH.ML-236A)
78. 3-(O-Benzoyl)-8'-(O-butyryl)-3',5'-dihydroxy-(DH.ML-236A)
79. 3-(O-Acetyl)-8'-(O-benzoyl)-3',5'-dihydroxy-(DH.ML-236A)
80. 3-(O-Phenylacetyl)-8'-(O-benzoyl)-3',5'-dihydroxy-(DH.ML-236A)
81. 3-(O-Acetyl)-8'-(O-phenylacetyl)-3',5'-dihydroxy-(DH.ML-236A)
82. 3-(O-Benzoyl)-8'-(O-phenylacetyl)-3',5'-dihydroxy-(DH.ML-236A)
83. 3,8'-Di(O-acetyl)-3',5'-dihydroxy-(DH.MB-530A)
84. 3,8'-Di(O-butyryl)-3',5'-dihydroxy-(DH.MB-530A)
85. 3-(O-2-Methylbutyryl)-3',5'-dihydroxy-(DH.MB-530B)
86. 3,8'-(O-stearoyl)-3',5'-dihydroxy-(DH.MB-530A)
87. 3,8'-Di(O-linolenoyl)-3',5'-dihydroxy-(DH.MB-530A)
88. 3,8'-Di(O-benzoyl)-3',5'-dihydroxy-(DH.MB-530A)
89. 3,8'-Di(O-phenylacetyl)-3',5'-dihydroxy-(DH.MB-530A)
90. 3,8'-Di(O-2-thienylacetyl)-3',5'-dihydroxy-(DH.MB-530A)

91. 3,8'-Di(O-2-thenoyl)-3',5'-dihydroxy-(DH.MB-530A)
92. 3-(O-Acetyl)-3',5'-dihydroxy-(DH.MB-530B)
93. 3-(O-Propionyl)-3',5'-dihydroxy-(DH.MB-530B)
94. 3-(O-Butyryl)-3',5'-dihydroxy-(DH.MB-530B)
95. 3-(O-Stearoyl)-3',5'-dihydroxy-(DH.MB-530B)
96. 3-(O-Linolenoyl)-3',5'-dihydroxy-(DH.MB-530B)
97. 3-(O-Benzoyl)-3',5'-dihydroxy-(DH.ML-236B)
98. 3-(O-Salicyloyl)-3',5'-dihydroxy-(DH.MB-530B)
99. 3-(O-Phenylacetyl)-3',5'-dihydroxy-(DH.MB-530B)
100. 3-(O-Cinnamoyl)-3',5'-dihydroxy-(DH.MB-530B)
101. 3-(O-2-Thenoyl)-3',5'-dihydroxy-(DH.MB-530B)
102. 3-(O-2-Thienylacetyl)-3',5'-dihydroxy-(DH.MB-530B)
103. 3-(O-Acetyl)-8'-(O-butyryl)-3',5'-dihydroxy-(DH.MB-530A)
104. 3-(O-Benzoyl)-8'-(O-butyryl)-3',5'-dihydroxy-(DH.MB-530A)
105. 3-(O-Acetyl)-8'-(O-benzoyl)-3',5'-dihydroxy-(DH.MB-530A)
106. 3-(O-Phenylacetyl)-8'-(O-benzoyl)-3',5'-dihydroxy-(DH.MB-530A)
107. 3-(O-Acetyl)-8'-(O-phenylacetyl)-3',5'-dihydroxy-(DH.MB-530A)
108. 3-(O-Benzoyl)-8'-(O-phenylacetyl)-3',5'-dihydroxy-(DH.MB-530A)
109. 3,8'-Di(O-acetyl)-3',5'-diacetoxy-(DH.ML-236A)
110. 3,8'-Di(O-acetyl)-3',5'-dibenzoyloxy-(DH.ML-236A)
111. 3,8'-Di(O-benzoyl)-3',5'-dibenzoyloxy-(DH.ML-236A)
112. 3-(O-Acetyl)-3',5'-diacetoxy-(DH.ML-236B)
113. 3,8'-Di(O-stearoyl)-3',5'-distearoyloxy-(DH.ML-236A)
114. 3-(O-Butyryl)-3',5'-dibutyryl-(DH.ML-236B)
115. 3-(O-Benzoyl)-3',5'-dibenzoyloxy-(DH.ML-236B)
116. 3,8'-Di(O-linolenoyl)-3',5'-dilinolenoyloxy-(DH.ML-236A)
117. 3-(O-Linolenoyl)-3',5'-dilinolenoyloxy-(DH.ML-236B)
118. 3-(O-Benzoyl)-3',5'-diacetoxy-(DH.ML-236B)
119. 3-(O-Propionyl)-3',5'-dipropionyloxy-(DH.ML-236B)
120. 3,8'-(O-Butyryloxy)-3',5'-dibutyryloxy-(DH.ML-236A)
121. 3,8'-Di(O-phenylacetyl)-3',5'-di(phenylacetyl)-(DH.ML-236A)
122. 3,8'-Di(O-acetyl)-3',5'-diacetoxy-(DH.MB-530A)
123. 3,8'-Di(O-acetyl)-3',5'-dibenzoyloxy-(DH.MB-530A)
124. 3,8'-Di(O-benzoyl)-3',5'-dibenzoyloxy-(DH.MB-530A)
125. 3-(O-Acetyl)-3',5'-diacetoxy-(DH.MB-530B)
126. 3,8'-Di(O-stearoyl)-3',5'-distearoyloxy-(DH.MB-530A)
127. 3-(O-Butyryl)-3',5'-dibutyryl-(DH.MB-530B)
128. 3-(O-Benzoyl)-3',5'-dibenzoyloxy-(DH.MB-530PB)
129. 3,8'-Di(O-linolenoyl)-3',5'-dilinolenoyloxy-(DH.MB-530A)
130. 3-(O-Linolenoyl)-3',5'-dilinolenoyloxy-(DH.MB-530B)
131. 3-(O-Benzoyl)-3',5'-diacetoxy-(DH.MB-530B)
132. 3-(O-Propionyl)-3',5'-dipropionyloxy-(DH.MB-530B)
133. 3,8'-(O-Butyryloxy)-3',5'-dibutyryloxy-(DH.MB-530A)
134. 3,8'-Di(O-phenylacetyl)-3',5'-di(phenylacetyl)-(DH.MB-530A)
135. 3'-Oxo-5'-hydroxy-(DH.ML-236A)
136. 3'-Oxo-5'-hydroxy-(DH.MB-530A)
137. 3-(O-Acetyl)-3'-oxo-5'-hydroxy-(DH.ML-236A)
138. 3-(O-Butyryl)-3'-oxo-5'-hydroxy-(DH.ML-236A)
139. 3-(O-Benzoyl)-3'-oxo-5'-hydroxy-(DH.ML-236A)
140. 3-(O-Acetyl)-3'-oxo-5'-hydroxy-(DH.MB-530A)
141. 3-(O-Butyryl)-3'-oxo-5'-hydroxy-(DH.MB-530A)
142. 3-(O-Benzoyl)-3'-oxo-5'-hydroxy-(DH.MB-530A)
143. 8'-(O-Acetyl)-3'-oxo-5'-hydroxy-(DH.ML-236A)
144. 8'-(O-Propionyl)-3'-oxo-5'-hydroxy-(DH.ML-236A)
145. 3'-Oxo-5'-hydroxy-(DH.ML-236B)
146. 8'-(O-Stearoyl)-3'-oxo-5'-hydroxy-(DH.ML-236A)
147. 8'-(O-Linolenoyl)-3'-oxo-5'-hydroxy-(DH.ML-236A)
148. 8'-(O-Benzoyl)-3'-oxo-5'-hydroxy-(DH.ML-236A)
149. 8'-(O-Salicyloyl)-3'-oxo-5'-hydroxy-(DH.ML-236A)
150. 8'-(O-Acetyl)-3'-oxo-5'-hydroxy-(DH.MB-530A)
151. 8'-(O-Propionyl)-3'-oxo-5'-hydroxy-(DH.MB-530A)
152. 3'-Oxo-5'-hydroxy-(DH.MB-530B)
153. 8'-(O-Stearoyl)-3'-oxo-5'-hydroxy-(DH.MB-530A)
154. 8'-(O-Linolenoyl)-3'-oxo-5'-hydroxy-(DH.MB-530A)
155. 8'-(O-Benzoyl)-3'-oxo-5'-hydroxy-(DH.MB-530A)
156. 8'-(O-Salicyloyl)-3'-oxo-5'-hydroxy-(DH.MB-530A)
157. 3,8'-Di(O-acetyl)-3'-oxo-5'-hydroxy-(DH.ML-236A)
158. 3,8'-Di(O-butyryl)-3'-oxo-5'-hydroxy-(DH.ML-236A)
159. 3-(O-2-Methylbutyryl)-3'-oxo-5'-hydroxy-(DH.ML-236B)
160. 3,8'-Di(O-benzoyl)-3'-oxo-5'-hydroxy-(DH.ML-236A)
161. 3,8'-Di(O-stearoyl)-3'-oxo-5'-hydroxy-(DH.ML-236A)
162. 3,8'-Di(O-linolenoyl)-3'-oxo-5'-hydroxy-(DH.ML-236A)
163. 3,8'-Di(O-acetyl)-3'-oxo-5'-hydroxy-(DH.MB-530A)
164. 3,8'-Di(O-butyryl)-3'-oxo-5'-hydroxy-(DH.MB-530A)
165. 3-(O-2-Methylbutyryl)-3'-oxo-5'-hydroxy-(DH.MB-530B)
166. 3,8'-Di(O-benzoyl)-3'-oxo-5'-hydroxy-(DH.MB-530A)
167. 3,8'-Di(O-stearoyl)-3'-oxo-5'-hydroxy-(DH.MB-530A)
168. 3,8'-Di(O-linolenoyl)-3'-oxo-5'-hydroxy-(DH.MB-530A)

169. 3,8'-Di(O-acetyl)-5'-acetoxy-3'-oxo-(DH.ML-236A)
170. 3,8'-Di(O-acetyl)-5'-propionyloxy-3'-oxo-(DH.ML-236A)
171. 3,8'-Di(O-acetyl)-5'-butyryloxy-3'-oxo-(DH.ML-236A)
172. 3,8'-Di(O-acetyl)-5'-stearoyloxy-3'-oxo-(DH.ML-236A)
173. 3,8'-Di(O-acetyl)-5'-linolenoyl-3'-oxo-(DH.ML-236A)
174. 3,8'-Di(O-acetyl)-5'-benzoyloxy-(DH.ML-236A)
175. 3,8'-Di(O-acetyl)-5'-(2-thenoyloxy)-3'-oxo-(DH.ML-236A)
176. 3,8'-Di(O-propionyl)-5'-acetoxy-3'-oxo-(DH.ML-236A)
177. 3,8'-Di(O-propionyl)-5'-butyryloxy-3'-oxo-(DH.ML-236A)
178. 3,8'-Di(O-propionyl)-5'-benzoyloxy-3'-oxo-(DH.ML-236A)
179. 3,8'-Di(O-propionyl)-5'-stearoyloxy-3'-oxo-(DH.ML-236A)
180. 3,8'-Di(O-butyryl)-5'-acetoxy-3'-oxo-(DH.ML-236A)
181. 3,8'-Di(O-butyryl)-5'-butyryloxy-3'-oxo-(DH.ML-236A)
182. 3,8'-Di(O-butyryl)-5'-linolenoyloxy-3'-oxo-(DH.ML-236A)
183. 3,8'-Di(O-butyryl)-5'-benzoyloxy-3'-oxo-(DH.ML-236A)
184. 3,8'-Di(O-stearoyl)-5'-acetoxy-3'-oxo-(DH.ML-236A)
185. 3,8'-Di(O-stearoyl)-5'-butyryloxy-3'-oxo-(DH.ML-236A)
186. 3,8'-Di(O-stearoyl)-5'-stearoyloxy-3'-oxo-(DH.ML-236A)
187. 3,8'-Di(O-stearoyl)-5'-linolenoyloxy-3'-oxo-(DH.ML-236A)
188. 3,8'-Di(O-stearoyl)-5'-benzoyloxy-3'-oxo-(DH.ML-236A)
189. 3,8'-Di(O-linolenoyl)-5'-acetoxy-3'-oxo-(DH.ML-236A)
190. 3,8'-Di(O-linolenoyl)-5'-propionyloxy-3'-oxo-(DH.ML-236A)
191. 3,8'-(O-Linolenoyl)-5'-butyryloxy-3'-oxo-(DH.ML-236A)
192. 3,8'-Di(O-linolenoyl)-5'-linolenoyloxy-3'-oxo-(DH.ML-236A)
193. 3,8'-Di(O-linolenoyl)-5'-benzoyloxy-3'-oxo-(DH.ML-236A)
194. 3,8'-Di(O-benzoyl)-5'-acetoxy-3'-oxo-(DH.ML-236A)
195. 3,8'-Di(O-benzoyl)-5'-propionyloxy-3'-oxo-(DH.ML-236A)
196. 3,8'-Di(O-benzoyl)-5'-butyryloxy-3'-oxo-(DH.ML-236A)
197. 3,8'-Di(O-benzoyl)-5'-stearoyloxy-3'-oxo-(DH.ML-236A)
198. 3,8'-Di(O-benzoyl)-5'-linolenoyloxy-3'-oxo-(DH.ML-236A)
199. 3,8'-Di(o-benzoyl)-5'-benzoyloxy-3'-oxo-(DH.ML-236A)
200. 3-(O-Acetyl)-5'-acetoxy-3'-oxo-(DH.ML-236B)
201. 3-(O-Acetyl)-5'-butyryloxy-3'-oxo-(DH.ML-236B)
202. 3-(O-Acetyl)-5'-stearoyloxy-3'-oxo-(DH.ML-236B)
203. 3-(O-Acetyl)-5'-benzoyloxy-3'-oxo-(DH.ML-236B)
204. 3-(O-Butyryl)-5'-acetoxy-3'-oxo-(DH.ML-236B)
205. 3-(O-Butyryl)-5'-butyryloxy-3'-oxo-(DH.ML-236B)
206. 3-(O-Butyryl)-5'-stearoyloxy-3'-oxo-(DH.ML-236B)
207. 3-(O-Butyryl)-5'-benzoyloxy-3'-oxo-(DH.ML-236B)
208. 3-(O-Stearoyl)-5'-acetoxy-3'-oxo-(DH.ML-236B)
209. 3-(O-Stearoyl)-5'-butyryloxy-3'-oxo-(DH.ML-236B)
210. 3-(O-Stearoyl)-5'-stearoyloxy-3'-oxo-(DH.ML-236B)
211. 3-(O-Stearoyl)-5'-linolenoyloxy-3'-oxo-(DH.ML-236B)
212. 3-(O-Linolenoyl)-5'-acetoxy-3'-oxo-(DH.ML-236B)
213. 3-(O-Linolenoyl)-5'-butyryloxy-3'-oxo-(DH.ML-236B)
214. 3-(O-Linolenoyl)-5'-stearoyloxy-3'-oxo-(DH.ML-236B)
215. 3-(O-Linolenoyl)-5'-linolenoyloxy-3'-oxo-(DH.ML-236B)
216. 3-(O-Butyryl)-8'-(O-acetyl)-5'-acetoxy-3'-oxo-(DH.ML-236A)
217. 3-(O-Butyryl)-8'-(O-acetyl)-5'-butyryloxy-3'-oxo-(DH.ML-236A)
218. 3-(O-Stearoyl)-8'-(O-acetyl)-5'-acetoxy-3'-oxo-(DH.ML-236A)
219. 3-(O-Stearoyl)-8'-(O-acetyl)-5'-stearoyloxy-3'-oxo-(DH.ML-236A)
220. 3-(O-Linolenoyl)-8'-(O-acetyl)-5'-linolenoyloxy-3'-oxo-(DH.ML-236A)
221. 3-(O-Benzoyl)-8'-(O-acetyl)-5'-benzoyloxy-3'-oxo-(DH.ML-236A)
222. 3,8'-Di(O-acetyl)-5'-acetoxy-3'-oxo-(DH.MB-530A)
223. 3,8'-Di(O-acetyl)-5'-propionyloxy-3'-oxo-(DH.MB-530A)
224. 3,8'-Di(O-acetyl)-5'-butyryloxy-3'-oxo-(DH.MB-530A)
225. 3,8'-Di(O-acetyl)-5'-stearoyloxy-3'-oxo-(DH.MB-530A)
226. 3,8'-Di(O-acetyl)-5'-linolenoyl-3'-oxo-(DH.MB-530A)
227. 3,8'-Di(O-acetyl)-5'-benzoyloxy-(DH.MB-530A)
228. 3,8'-Di(O-acetyl)-5'-(2-thenoyloxy)-3'-oxo-(DH.MB-530A)
229. 3,8'-Di(O-propionyl)-5'-acetoxy-3'-oxo-(DH.MB-530A)
230. 3,8'-Di(O-propionyl)-5'-propionyloxy-3'-oxo-(DH.MB-530A)
231. 3,8'-Di(O-propionyl)-5'-butyryloxy-3'-oxo(DH-MB-530A)
232. 3,8'-Di(O-propionyl)-5'-benzoyloxy-3'-oxo-(DH.MB-530A)
233. 3,8'-Di(O-propionyl)-5'-stearoyloxy-3'-oxo-(DH.MB-236A)
234. 3,8'-Di(O-butyryl)-5'-acetoxy-3'-oxo-(DH.MB-530A)
235. 3,8'-Di(O-butyryl)-5'-butyryloxy-3'-oxo-(DH.MB-530A)
236. 3,8'-Di(O-butyryl)-5'-linolenoyloxy-3'-oxo-(DH.MB-530A)
237. 3,8'-Di(O-butyryl)-5'-benzoyloxy-3'-oxo-(DH.MB-530A)

238. 3,8'-Di(O-stearoyl)-5'-acetoxy-3'-oxo-(DH.MB-530A)
239. 3,8'-Di(O-stearoyl)-5'-butyryloxy-3'-oxo-(DH.MB-530A)
240. 3,8'-Di(O-stearoyl)-5'-stearoyloxy-3'-oxo-(DH.MB-530A)
241. 3,8'-Di(O-stearoyl)-5'-linolenoyloxy-3'-oxo-(DH.MB-530A)
242. 3,8'-Di(O-stearoyl)-5'-benzoyloxy-3'-oxo-(DH.MB-530A)
243. 3,8'-Di(O-linolenoyl)-5'-acetoxy-3'-oxo-(DH.MB-530A)
244. 3,8'-Di(O-linolenoyl)-5'-propionyloxy-3'-oxo-(DH.MB-530A)
245. 3,8'-Di(O-linolenoyl)-5'-butyryloxy-3'-oxo-(DH.MB-530A)
246. 3,8'-Di(O-linolenoyl)-5'-linolenoyloxy-3'-oxo-(DH.MB-530A)
247. 3,8'-Di(O-linolenoyl)-5'-benzoyloxy-3'-oxo-(DH.MB-530A)
248. 3,8'-Di(O-benzoyl)-5'-acetoxy-3'-oxo-(DH.MB-530A)
249. 3,8'-Di(O-benzoyl)-5'-propionyloxy-3'-oxo-(DH.MB-530A)
250. 3,8'-Di(O-benzoyl)-5'-butyryloxy-3'-oxo-(DH.MB-530A)
251. 3,8'-Di(O-benzoyl)-5'-stearoyloxy-3'-oxo-(DH.MB-530A)
252. 3,8'-Di(O-benzoyl)-5'-linolenoyloxy-3'-oxo-(DH.MB-530A)
253. 3,8'-Di(O-benzoyl)-5'-benzoyloxy-3'-oxo-(DH.MB-530A)
254. 3-(O-Acetyl)-5'-acetoxy-3'-oxo-(DH.MB-530B)
255. 3-(O-Acetyl)-5'-butyryloxy-3'-oxo-(DH.MB-530B)
256. 3-(O-Acetyl)-5'-stearoyloxy-3'-oxo-(DH.MB-530B)
257. 3-(O-Acetyl)-5'-benzoyloxy-3'-oxo-(DH.MB-530B)
258. 3-(O-Butyryl)-5'-acetoxy-3'-oxo-(DH.MB-530B)
259. 3-(O-Butyryl)-5'-butyryloxy-3'-oxo-(DH.MB-530B)
260. 3-(O-Butyryl)-5'-stearoyloxy-3'-oxo-(DH.MB-530B)
261. 3-(O-Butyryl)-5'-benzoyloxy-3'-oxo-(DH.MB-530B)
262. 3-(O-Stearoyl)-5'-acetoxy-3'-oxo-(DH.MB-530B)
263. 3-(O-Stearoyl)-5'-butyryloxy-3'-oxo-(DH.MB-530B)
264. 3-(O-Stearoyl)-5'-stearoyloxy-3'-oxo-(DH.MB-530B)
265. 3-(O-Stearoyl)-5'-linolenoyloxy-3'-oxo-(DH.MB-530B)
266. 3-(O-Linolenoyl)-5'-acetoxy-3'-oxo-(DH.MB-530B)
267. 3-(O-Linolenoyl)-5'-butyryloxy-3'-oxo-(DH.MB-530B)
268. 3-(O-Linolenoyl)-5'-stearoyloxy-3'-oxo-(DH.MB-530B)
269. 3-(O-Linolenoyl)-5'-linolenoyloxy-3'-oxo-(DH.MB-530B)
270. 3-(O-Butyryl)-8'-(O-acetyl)-5'-acetoxy-3'-oxo-(DH.MB-530A)
271. 3-(O-Butyryl)-8'-(O-acetyl)-5'-butyryloxy-3'-oxo-(DH.MB-530A)
272. 3-(O-Stearoyl)-8'-(O-acetyl)-5'-acetoxy-3'-oxo-(DH.MB-530A)
273. 3-(O-Stearoyl)-8'-(O-acetyl)-5'-stearoyloxy-3'-oxo-(DH.MB-530A)
274. 3-(O-Linolenoyl)-8'-(O-acetyl)-5'-linolenoyloxy-3'-oxo-(DH.MB-530A)
275. 3-(O-Benzoyl)-8'-(O-acetyl)-5'-benzoyloxy-3'-oxo-(DH.MB-530A)
276. 3,8'-Di(O-acetyl)-3',5'-dioxo-(DH.ML-236A)
277. 3,8'-Di(O-butyryl)-3',5'-dioxo-(DH.ML-236A)
278. 3-(O-2-Methylbutyryl)-3',5'-dioxo-(DH.ML-236B)
279. 3,8'-Di(O-stearoyl)-3',5'-dioxo-(DH.ML-236A)
280. 3,8'-Di(O-linolenoyl)-3',5'-dioxo-(DH.ML-236A)
281. 3,8'-Di(O-benzoyl)-3',5'-dioxo-(DH.ML-236A)
282. 3,8'-Di(O-phenylacetyl)-3',5'-dioxo-(DH.ML-236A)
283. 3,8'-Di(O-2-thienylacetyl)-3',5'-dioxo-(DH.ML-236A)
284. 3,8'-Di(O-2-thenoyl)-3',5'-dioxo-(DH.ML-236A)
285. 3-(O-Acetyl)-3',5'-dioxo-(DH.ML-236B)
286. 3-(O-Propionyl)-3',5'-dioxo-(DH.ML-236B)
287. 3-(O-Butyryl)-3',5'-dioxo-(DH.ML-236B)
288. 3-(O-Stearoyl)-3',5'-dioxo-(DH.ML-236B)
289. 3-(O-Linolenoyl)-3',5'-dioxo-(DH.ML-236B)
290. 3-(O-Benzoyl)-3',5'-dioxo-(DH.ML-236B)
291. 3-(O-Salicyloyl)-3',5'-dioxo-(DH.ML-236B)
292. 3-(O-Phenylacetyl)-3',5'-dioxo-(DH.ML-236B)
293. 3-(O-Cinnamoyl)-3',5'-dioxo-(DH.ML-236B)
294. 3-(O-2-Thenoyl)-3',5'-dioxo-(DH.ML-236B)
295. 3-(O-2-Thienylacetyl)-3',5'-dioxo-(DH.ML-236B)
296. 3-(O-Acetyl)-8'-(O-butyryl)-3',5'-dioxo-(DH.ML-236A)
297. 3-(O-Benzoyl)-8'-(O-butyryl)-3',5'-dioxo-(DH.ML-236A)
298. 3-(O-Acetyl)-8'-(O-benzoyl)-3',5'-dioxo-(DH.ML-236A)
299. 3-(O-Phenylacetyl)-8'-(O-benzoyl)-3',5'-dioxo-(DH.ML-236A)
300. 3-(O-Acetyl)-8'-(O-phenylacetyl)-3',5'-dioxo-(DH.ML-236A)
301. 3-(O-Benzoyl)-8'-(O-phenylacetyl)-3',5'-dioxo-(DH.ML-236A)
302. 3,8'-Di(O-acetyl)-3',5'-dioxo-(DH.MB-530A)
303. 3,8'-Di(O-butyryl)-3',5'-dioxo-(DH.MB-530A)
304. 3-(O-2-Methylbutyryl)-3',5'-dioxo-(DH.MB-530B)
305. 3,8'-Di(O-stearoyl)-3',5'-dioxo-(DH.MB-530A)
306. 3,8'-Di(O-linolenoyl)-3',5'-dioxo-(DH.MB-530A)
307. 3,8'-Di(O-benzoyl)-3',5'-dioxo-(DH.MB-530A)
308. 3,8'-Di(O-phenylacetyl)-3',5'-dioxo-(DH.MB-530A)
309. 3,8'-Di(O-2-thienylacetyl)-3',5'-dioxo-(DH.MB-530A)
310. 3,8'-Di(O-2-thenoyl)-3',5'-dioxo-(DH.MB-530A)
311. 3-(O-Acetyl)-3',5'-dioxo-(DH.MB-530B)
312. 3-(O-Propionyl)-3',5'-dioxo-(DH.MB-530B)
313. 3-(O-Butyryl)-3',5'-dioxo-(DH.MB-530B)
314. 3-(O-Stearoyl)-3',5'-dioxo-(DH.MB-530B)
315. 3-(O-Linolenoyl)-3',5'-dioxo-(DH.MB-530B)
316. 3-(O-Benzoyl)-3',5'-dioxo-(DH.ML-236B)
317. 3-(O-Salicyloyl)-3',5'-dioxo-(DH.MB-530B)
318. 3-(O-Phenylacetyl)-3',5'-dioxo-(DH.MB-530B)
319. 3-(O-Cinnamoyl)-3',5'-dioxo-(DH.MB-530B)
320. 3-(O-2-Thenoyl)-3',5'-dioxo-(DH.MB-530B)
321. 3-(O-2-Thienylacetyl)-3',5'-dioxo-(DH.MB-530B)

322. 3-(O-Acetyl)-8'-(O-butyryl)-3',5'-dioxo-(DH.MB-530A)
323. 3-(O-Benzoyl)-8'-(O-butyryl)-3',5'-dioxo-(DH.MB-530A)
324. 3-(O-Acetyl)-8'-(O-benzoyl)-3',5'-dioxo-(DH.MB-530A)
325. 3-(O-Phenylacetyl)-8'-(O-benzoyl)-3',5'-dioxo-(DH.MB-530A)
326. 3-(O-Acetyl)-8'-(O-phenylacetyl)-3',5'-dioxo-(DH.MB-530A)
327. 3-(O-Benzoyl)-8'-(O-phenylacetyl)-3',5'-dioxo-(DH.MB-530A)
328. 3'-Perhydroxy-5'-hydroxy-(DH.ML-236A)
329. 3'-Perhydroxy-5'-hydroxy-(DH.ML-236B)
330. 3'-Perhydroxy-5'-hydroxy-(DH.MB-530A)
331. 3'-Perhydroxy-5'-hydroxy-(DH.MB-530B)
332. 3',5'-Dihydroxy-(TH.ML-236A)
333. 3',5'-Dihydroxy-(TH.MB-530A)
334. 3',5'-Dihydroxy-(TH.ML-230B)
335. 3',5'-Dihydroxy-(TH.MB-530B)
336. 3,8'-Di(O-acetyl)-3',5'-diacetoxy-(TH.ML-236A)
337. 3,8'-Di(O-propionyl)-3',5'-dipropionyloxy-(TH.ML-236A)
338. 3,8'-Di(O-butyryl)-3',5'-dibutyryloxy-(TH.ML-236A)
339. 3-(O-Acetyl)-3',5'-diacetoxy-(TM.ML-236B)
340. 3-(O-Propionyl)-3',5'-dipropionyloxy-(TH.ML-236B)
341. 3-(O-Butyryl)-3',5'-dibutyryloxy-(TH.ML-236B)
342. 3,8'-Di(O-acetyl)-3',5'-diacetoxy-(TH.MB-530A)
343. 3,8'-Di(O-propionyl)-3',5'-dipropionyloxy-(TH.MB-530A)
344. 3,8'-Di(O-butyryl)-3',5'-dibutyryloxy-(TH.MB-530A)
345. 3-(O-Acetyl)-3',5'-diacetoxy-(TH.MB-530B)
346. 3-(O-Butyryl)-3',5'-dibutyryloxy-(TH.MB-530B)
347. 3-(O-Propionyl)-3',5'-dipropionyloxy-(TH.MB-530B)
348. 3',5'-Dihydroxy-(DH.ML-236A-carboxylic acid)
349. Sodium 3',5'-dihydroxy-(DH.ML-236A-carboxylate)
350. Calcium bis[3',5'-dihydroxy-(DH.ML-236A-carboxylate)]
351. 3',5'-Dihydroxy-(DH.MB-530A-carboxylic acid)
352. Sodium 3',5'-dihydroxy-(DH.MB-530A-carboxylate)
353. Aluminium tris[3',5'-dihydroxy-(DH.MB-530A-carboxylate)]
354. Methyl 3',5'-dihydroxy-(DH.ML-236A-carboxylate)
355. Ethyl 3',5'-dihydroxy-(DH.ML-236A-carboxylate)
356. Benzyl 3',5'-(DH.ML-236A-carboxylate)
357. Phenacyl 3',5'-dihydroxy-(DH.ML-236A-carboxylate)
358. p-Methoxyphenacyl 3',5'-dihydroxy-(DH.ML-236A-carboxylate)
359. Pivaloyloxymethyl 3',5'-dihydroxy-(DH.ML-236A-carboxylate)
360. Methyl 3',5'-dihydroxy-(DH.MB-530A-carboxylate)
361. Ethyl 3',5'-dihydroxy-(DH.MB-530A-carboxylate)
362. Benzyl 3',5'-dihydroxy-(DH.MB-530A-carboxylate)
363. Phenacyl 3',5'-dihydroxy-(DH.MB-530A-carboxylate)
364. p-Methoxyphenacyl 3',5'-dihydroxy-(DH.MB-530A-carboxylate)
365. Pivaloyloxymethyl 3',5'-dihydroxy-(DH.MB-530A-carboxylate)
366. 3',5'-Dihydroxy-(TH.ML-236A-carboxylic acid)
367. Sodium 3',5'-dihydroxy-(TH.ML-236A-carboxylate)
368. Methyl 3',5'-dihydroxy-(TH.ML-236A-carboxylate)
369. Ethyl 3',5'-dihydroxy-(TH.ML-236A-carboxylate)
370. Pivaloyloxymethyl 3',5'-dihydroxy-(TH.ML-236A-carboxylate)
371. Phenacyl 3',5'-dihydroxy-(TH.ML-236A-carboxylate)
372. Acetoxymethyl 3',5'-dihydroxy-(TH.ML-236A-carboxylate)
373. 3',5'-Dihydroxy-(TH.ML-236B-carboxylic acid)
374. Sodium 3',5'-dihydroxy-(TH.ML-236B-carboxylate)
375. Methyl 3',5'-dihydroxy-(TH.ML-236B-carboxylate)
376. Ethyl 3',5'-dihydroxy-(TH.ML-236B-carboxylate)
377. Pivaloyloxymethyl 3',5'-dihydroxy-(TH.ML-236B-carboxylate)
378. Phenacyl 3',5'-dihydroxy-(TH.ML-236B-carboxylate)
379. Acetoxymethyl 3',5'-dihydroxy-(TH.ML-236A-carboxylate)
380. 3',5'-Dihydroxy-(TH.MB-530A-carboxylic acid)
381. Sodium 3',5'-dihydroxy-(TH.MB-530A-carboxylate)
382. Methyl 3',5'-dihydroxy-(TH.ML-530A-carboxylate)
383. Ethyl 3',5'-dihydroxy-(TH.MB-530A-carboxylate)
384. Pivaloyloxymethyl 3',5'-dihydroxy-(TH.MB-530A-carboxylate)
385. Phenacyl 3',5'-dihydroxy-(TH.MB-530A-carboxylate)
386. Acetoxymethyl 3',5'-dihydroxy-(TH.MB-530A-carboxylate)
387. 3',5'-Dihydroxy-(TH.MB-530B-carboxylic acid)
388. Sodium 3',5'-dihydroxy-(TH.MB-530B-carboxylate)
389. Methyl 3',5'-dihydroxy-(TH.MB-530B-carboxylate)
390. Ethyl 3',5'-dihydroxy-(TH.MB-530B-carboxylate)
391. Pivaloyloxymethyl-3',5'-dihydroxy-(TH.MB-530B-carboxylate)
392. Phenacyl 3',5'-dihydroxy-(TH.MB-530B-carboxylate)
393. Acetoxymethyl 3',5'-dihydroxy-(TH.MB-530B-carboxylate)
394. 3,5,8'-Tri(O-acetyl)-3',5'-diacetoxy-(TH.ML-236A-carboxylic acid)
395. Sodium 3,5,8'-tri(O-acetyl)-3',5'-diacetoxy-(TH.ML-236A-carboxylate)
396. Methyl 3,5,8'-tri(O-acetyl)-3',5'-diacetoxy-(TH.ML-236A-carboxylate)
397. 3,5-Di(O-acetyl)-3', 5'-diacetoxy-(TH.ML-236B-carboxylic acid)

398. Sodium 3,5-di(O-acetyl)-3',5'-diacetoxy-(TH.ML-236B-carboxylate)
399. Methyl 3,5-di(O-acetyl)-3',5'-diacetoxy-(TH.ML-236B-carboxylate)
400. Ethyl 3,5-di(O-acetyl)-3',5'-diacetoxy-(TH.ML-236B-carboxylate)
401. Acetoxymethyl 3,5-di(O-acetyl)-3',5'-diacetoxy-(TH.ML-236B-carboxylate)
402. Pivaloyloxymethyl 3,5-di(O-acetyl)-3',5'-diacetoxy-(TH.ML-236B-carboxylate)
403. Methyl 3,5-di(O-propionyl)-3',5'-dipropionyloxy-(TH.ML-236B-carboxylate)
404. 3,5,8'-Tri(O-acetyl)-3',5'-diacetoxy-(TH.MB-530A-carboxylic acid)
405. Sodium 3,5,8'-tri(O-acetyl)-3',5'-diacetoxy-(TH.MB-530A-carboxylate)
406. Methyl 3,5,8'-tri(O-acetyl)-3',5'-diacetoxy-(TH.MB-530A-carboxylate)
407. 3,5-Di(O-acetyl)-3',5'-diacetoxy-(TH.MB-530B-carboxylic acid)
408. Sodium 3,5-di(O-acetyl)-3',5'-diacetoxy-(TH.MB-530B-carboxylate)
409. Methyl 3,5-di(O-acetyl)-3',5'-diacetoxy-(TH.MB-530B-carboxylate)
410. Ethyl 3,5-di(O-acetyl)-3',5'-diacetoxy-(TH.MB-530B-carboxylate)
411. Acetoxymethyl 3,5-di(O-acetyl)-3',5'-diacetoxy-(TH.MB-530B-carboxylate)
412. Pivaloyloxymethyl 3,5-di(O-acetyl)-3',5'-diacetoxy-(TH.MB-530B-carboxylate)
413. Methyl 3,5-di(O-propionyl)-3',5'-dipropionyloxy-(TH.MB-530B-carboxylate)
414. Sodium 8'-(O-acetyl)-3',5'-dihydroxy-(DH.ML-236A-carboxylate)
415. Methyl 8'-(O-acetyl)-3',5'-dihydroxy-(DH.ML-236A-carboxylate)
416. Ethyl 8'-(O-acetyl)-3',5'-dihydroxy-(DH.ML-236A-carboxylate)
417. Sodium 8'-(O-propionyl)-3',5'-dihydroxy-(DH.ML-236A-carboxylate)
418. Methyl 8'-(O-propionyl)-3',5'-dihydroxy-(DH.ML-236A-carboxylate)
419. Ethyl 8'-(O-propionyl)-3',5'-dihydroxy-(DH.ML-236A-carboxylate)
420. 3',5'-Dihydroxy-(DH.ML-236B-carboxylic acid)
421. Sodium 3',5'-dihydroxy-(DH.ML-236B-carboxylate)
422. Potassium 3',5'-dihydroxy-(DH.ML-236B-carboxylate)
423. Calcium bis[3',5'-dihydroxy-(DH.ML-236B-carboxylate)]
424. Aluminium tris[3',5'-dihydroxy-(DH.ML-236B-carboxylate)]
425. Methyl 3',5'-dihydroxy-(DH.ML-236B-carboxylate)
426. Ethyl 3',5'-dihydroxy-(DH.ML-236B-carboxylate)
427. Butyl 3',5'-dihydroxy-(DH.ML-236B-carboxylate)
428. Phenacyl 3',5'-dihydroxy-(DH.ML-236B-carboxylate)
429. p-Methoxyphenacyl 3',5'-dihydroxy-(DH.ML-236B-carboxylate)
430. Benzyl 3',5'-dihydroxy-(DH.ML-236B-carboxylate)
431. Pivaloyloxymethyl 3',5'-dihydroxy-(DH.ML-236B-carboxylate)
432. 8'-(O-Stearoyl)-3',5'-dihydroxy-(DH.ML-236A-carboxylic acid)
433. Sodium 8'-(O-stearoyl)-3',5'-dihydroxy-(DH.ML-236A-carboxylate)
434. Methyl 8'-(O-stearoyl)-3',5'-dihydroxy-(DH.ML-236A-carboxylate)
435. 8'-(O-Linolenoyl)-3',5'-dihydroxy-(DH.ML-236A-carboxylic acid)
436. Methyl 8'-(O-linolenoyl)-3',5'-dihydroxy-(DH.ML-236A-carboxylate)
437. 8'-(O-Benzoyl)-3',5'-dihydroxy-(DH.ML-236A-carboxylic acid)
438. Sodium 8'-(O-benzoyl)-3',5'-dihydroxy-(DH.ML-236A-carboxylate)
439. Methyl 8'-(O-benzoyl)-3',5'-dihydroxy-(DH.ML-236A-carboxylate)
440. 8'-(O-Cinnamoyl)-3',5'-dihydroxy-(DH.ML-236A-carboxylic acid)
441. Sodium 8'-(O-cinnamoyl)-3',5'-dihydroxy-(DH.ML-236A-carboxylate)
442. Methyl 8'-(O-cinnamoyl)-3',5'-dihydroxy-(DH.ML-236A-carboxylate)
443. 3-(O-Acetyl)-3',5'-dihydroxy-(DH.ML-236A-carboxylic acid)
444. Sodium 3-(O-acetyl)-3',5'-dihydroxy-(DH.ML-236A-carboxylate)
445. Methyl 3-(O-acetyl)-3',5'-dihydroxy-(DH.ML-236A-carboxylate)
446. 3-(O-Acetyl)-3',5'-dihydroxy-(DH.ML-236B-carboxylic acid)
447. Sodium 3-(O-acetyl)-3',5'-dihydroxy-(DH.ML-236B-carboxylate)
448. Methyl 3-(O-acetyl)-3',5'-dihydroxy-(DH.ML-236B-carboxylate)
449. Sodium 8'-(O-acetyl)-3',5'-dihydroxy-(DH.MB-530A-carboxylate)
450. Methyl 8'-(O-acetyl)-3',5'-dihydroxy-(DH.MB-530A-carboxylate)
451. Ethyl 8'-(O-acetyl)-3',5'-dihydroxy-(DH.MB-530A-carboxylate)
452. Sodium 8'-(O-propionyl)-3',5'-dihydroxy-(DH.MB-530A-carboxylate)
453. Methyl 8'-(O-propionyl)-3',5'-dihydroxy-(DH.MB-530A-carboxylate)
454. Ethyl 8'-(O-propionyl)-3',5'-dihydroxy-(DH.MB-530A-carboxylate)
455. 3',5'-Dihydroxy-(DH.MB-530B-carboxylic acid)
456. Sodium 3',5'-dihydroxy-(DH.MB-530B-carboxylate)
457. Potassium 3',5'-dihydroxy-(DH.MB-530B-carboxylate)
458. Calcium bis[3',5'-dihydroxy-(DH.MB-530B-carboxylate)]
459. Aluminium tris[3',5'-dihydroxy-(DH.MB-530B-carboxylate)]
460. Methyl 3',5'-dihydroxy-(DH.MB-530B-carboxylate)
461. Ethyl 3',5'-dihydroxy-(DH.ML-236B-carboxylate)
462. Butyl 3',5'-dihydroxy-(DH.ML-236B-carboxylate)
463. Phenacyl 3',5'-dihydroxy-(DH.ML-236B-carboxylate)
464. p-Methoxyphenacyl 3',5'-dihydroxy-(DH.ML-236B-carboxylate)
465. Benzyl 3',5'-dihydroxy-(DH.ML-236B-carboxylate)

466. Pivaloyloxymethyl 3',5'-dihydroxy-(DH.ML-236B-carboxylate)
467. 8'-(O-Stearoyl)-3',5'-dihydroxy-(DH.ML-236A-carboxylic acid)
468. Sodium 8'-(O-stearoyl)-3',5'-dihydroxy-(DH.ML-236A-carboxylate)
469. Methyl 8'-(O-stearoyl)-3',5'-dihydroxy-(DH.ML-236A-carboxylate)
470. 8'-(O-Linolenoyl)-3',5'-dihydroxy-(DH.ML-236A-carboxylic acid)
471. Methyl 8'-(O-linolenoyl)-3',5'-dihydroxy-(DH.ML-236A-carboxylate)
472. 8'-(O-Benzoyl)-3',5'-dihydroxy-(DH.ML-236A-carboxylic acid)
473. Sodium 8'-(O-benzoyl)-3',5'-dihydroxy-(DH.ML-236A-carboxylate)
474. Methyl 8'-(O-benzoyl)-3',5'-dihydroxy-(DH.ML-236A-carboxylate)
475. 8'-(O-Cinnamoyl)-3',5'-dihydroxy-(DH.ML-236A-carboxylic acid)
476. Sodium 8'-(O-cinnamoyl)-3',5'-dihydroxy-(DH.ML-236A-carboxylate)
477. Methyl 8'-(O-cinnamoyl)-3',5'-dihydroxy-(DH.ML-236A-carboxylate)
478. 3-(O-Acetyl)-3',5'-dihydroxy-(DH.ML-236A-carboxylic acid)
479. Sodium 3-(O-acetyl)-3',5'-dihydroxy-(DH.ML-236A-carboxylate)
480. Methyl 3-(O-acetyl)-3',5'-dihydroxy-(DH.ML-236A-carboxylate)
481. 3-(O-Acetyl)-3',5'-dihydroxy-(DH.ML-236B-carboxylic acid)
482. Sodium 3-(O-acetyl)-3',5'-dihydroxy-(DH.ML-236B-carboxylate)
483. Methyl 3-(O-acetyl)-3',5'-dihydroxy-(DH.-ML-236B-carboxylate)
484. 3,5,8'-Tri(O-acetyl)-3',5'-diacetoxy-(DH.ML-236A-carboxylic acid)
485. Sodium 3,5,8'-tri(O-acetyl)-3',5'-diacetoxy-(DH.ML-236A-carboxylate)
486. Potassium 3,5,8'-tri(O-acetyl)-3',5'-diacetoxy-(DH.ML-236A-carboxylate)
487. Calcium bis[3,5,8'-tri(O-acetyl)-3',5'-diacetoxy-(DH.ML-236A-carboxylate)]
488. Methyl 3,5,8'-tri(O-acetyl)-3',5'-diacetoxy-(DH.ML-236A-carboxylate)
489. Ethyl 3,5,8'-tri(O-acetyl)-3',5'-diacetoxy-(DH.ML-236A-carboxylate)
490. 3,5,8'-Tri(O-propionyl)-3',5'-dipropionyloxy-(DH.ML-236A-carboxylic acid)
491. Sodium 3,5,8'-tri(O-propionyl)-3',5'-dipropionyloxy-(DH.ML-236A-carboxylate)
492. Methyl 3,5,8'-tri(O-propionyl)-3',5'-dipropionyloxy-(DH.ML-236A-carboxylate)
493. 3,5,8'-Tri(O-stearoyl)-3',5'-distearoyloxy-(DH.ML-236A-carboxylic acid)
494. Sodium 3,5,8'-tri(O-stearoyl)-3',5'-distearoyloxy-(DH.ML-236A-carboxylate)
495. Methyl 3,5,8'-tri(O-stearoyl)-3',5'-distearoyloxy-(DH.ML-236A-carboxylate)
496. Ethyl 3,5,8'-tri(O-stearoyl)-3',5'-distearoyloxy-(DH.ML-236A-carboxylate)
497. Butyl 3,5,8'-tri(O-stearoyl)-3',5'-distearoyloxy-(DH.ML-236A-carboxylate)
498. 3,5,8'-Tri(O-linolenoyl)-3',5'-dilinolenoyloxy-(DH.ML-236A-carboxylic acid)
499. Sodium 3,5,8'-tri(O-linolenoyl)-3',5'-dilinolenoyl-oxy-(DH.ML-236A-carboxylate)
500. Methyl 3,5,8'-tri(O-linolenoyl)-3',5'-dilinolenoyloxy-(DH.ML-236A-carboxylate)
501. Pivaloyloxymethyl 3,5,8'-tri(O-linolenoyl)-3',5'-dilinolenoyloxy-(DH.ML-236A-carboxylate)
502. 3,5-Di(O-acetyl)-3',5'-diacetoxy-(DH.ML-236B-carboxylic acid)
503. Sodium 3,5-di(O-acetyl)-3',5'-diacetoxy-(DH.ML-236B-carboxylate)
504. Potassium 3,5-di(O-acetyl)-3',5'-diacetoxy-(DH.ML-236B-carboxylate)
505. Calcium bis[3,5-di(O-acetyl)-3',5'-diacetoxy-(DH.ML-236B -carboxylate)]
506. Aluminium tris[3,5-di(O-acetyl)-3',5'-diacetoxy-(DH.ML-236B-carboxylate)]
507. Methyl 3,5-di(O-acetyl)-3',5'-diacetoxy-(DH.ML-236B-carboxylate)
508. Ethyl 3,5-di(O-acetyl)-3',5'-diacetoxy-(DH.ML-236B-carboxylate)
509. Butyl 3,5-di(O-acetyl)-3',5'-diacetoxy-(DH.ML-236B-carboxylate)
510. Pivaloyloxymethyl 3,5-di(O-acetyl)-3',5'-diacetoxy-(DH.ML-236B-carboxylate)
511. Methoxymethyl 3,5-di(O-acetyl)-3',5'-diacetoxy-(DH.ML-236B-carboxylate)
512. Phenacyl 3,5-di(O-acetyl)-3',5'-diacetoxy-(DH.ML-236B-carboxylate)
513. 3,5-Di(O-butyryl)-3',5'-dibutyryloxy-(DH.ML-236B-carboxylic acid)
314. Sodium 3,5-di(O-butyryl)-3',5'-dibutyryloxy-(DH.ML-236B-carboxylate)
515. Methyl 3,5-di(O-butyryl)-3',5'-dibutyryloxy-(DH.ML-236B-carboxylate)
516. 3,5-Di(O-stearoyl)-3',5'-distearoyloxy-(DH.ML-236B-carboxylic acid)
517. Methyl 3,5-di(O-stearoyl)-3',5'-distearoyloxy-(DH.ML-236B-carboxylate)
518. 3,5-Di(O-linolenoyl)-3',5'-dilinolenoyloxy-(DH.ML-236B-carboxylic acid)
519. Sodium 3,5-di(O-linolenoyl)-3',5'-dilinolenoyloxy-(DH.ML-236B-carboxylate)
520. 3,5-Di(O-thienylacetyl)-3',5'-dithienylacetyl-(DH.ML-236B-carboxylic acid)
521. 3,5,8'-Tri(O-acetyl)-3',5'-diacetoxy-(DH.MB-530A-carboxylic acid)
522. Sodium 3,5,8'-tri(O-acetyl)-3',5'-diacetoxy-(DH.MB-530A-carboxylate)
523. Potassium 3,5,8'-tri(O-acetyl)-3',5'-diacetoxy-(DH.MB-530A-carboxylate)
524. Calcium bis[3,5,8'-tri(O-acetyl)-3',5'-diacetoxy-(DH.MB-530A-carboxylate)]
525. Methyl 3,5,8'-tri(O-acetyl)-3',5'-diacetoxy-(DH.MB-530A-carboxylate)
526. Ethyl 3,5,8'-tri(O-acetyl)-3',5'-diacetoxy-(DH.MB-530A-carboxylate)
527. 3,5,8'-Tri(O-propionyl)-3',5'-dipropionyloxy-(DH.MB-530A-carboxylic acid)
528. Sodium 3,5,8'-tri(O-propionyl)-3',5'-dipropionyloxy-(DH.MB-530A-carboxylate)
529. Methyl 3,5,8'-tri(O-propionyl)-3',5'-dipropionyloxy-(DH.MB-530A-carboxylate)
530. 3,5,8'-Tri(O-stearoyl)-3',5'-distearoyloxy-(DH.MB-530A-carboxylic acid)
531. Sodium 3,5,8'-tri(O-stearoyl)-3',5'-distearoyloxy-(DH.MB-530A-carboxylate)
532. Methyl 3,5,8'-tri(O-stearoyl)-3',5'-distearoyloxy-(DH.MB-530A-carboxylate)
533. Ethyl 3,5,8'-tri(O-stearoyl)-3',5'-distearoyloxy-(DH.MB-530A-carboxylate)

534. Butyl 3,5,8'-tri(O-stearoyl)-3',5'-distearoyloxy-(DH.MB-530A-carboxylate)
535. 3,5,8'-Tri(O-linolenoyl)-3',5'-dilinolenoyloxy-(DH.MB-530A-carboxylic acid)
536. Sodium 3,5,8'-tri(O-linolenoyl)-3',5'-dilinolenoyloxy-(DH.MB-530A-carboxylate)
537. Methyl 3,5,8'-tri(O-linolenoyl)-3',5'-dilinolenoyloxy(DH.MB-530A-carboxylate)
538. Pivaloyloxymethyl 3,5,8'-tri(O-linolenoyl)-3',5'-dilinolenoyloxy-(DH.MB-530A-carboxylate)
539. 3,5-Di(O-acetyl)-3',5'-diacetoxy-(DH.MB-530B-carboxylic acid)
540. Sodium 3,5-di(O-acetyl)-3',5'-diacetoxy-(DH.MB-530B-carboxylate)
541. Potassium 3,5-di(O-acetyl)-3',5'-diacetoxy-(DH.MB-530B-carboxylate)
542. Calcium bis[3,5-di(O-acetyl)-3',5'-diacetoxy-(DH.MB-530B-carboxylate)]
543. Aluminium tris[3,5-di(O-acetyl)-3',5'-diacetoxy-(DH.MB-530B-carboxylate)]
544. Methyl 3,5-di(O-acetyl)-3',5'-diacetoxy-(DH.MB-530B-carboxylate)
545. Ethyl 3,5-di(O-acetyl)-3',5'-diacetoxy-(DH.MB-530B-carboxylate)
546. Butyl 3,5-di(O-acetyl)-3',5'-diacetoxy-(DH.MB-530B-carboxylate)
547. Pivaloyloxymethyl 3,5-di(O-acetyl)-3',5'-diacetoxy-(DH.MB-530B-carboxylate)
548. Methoxymethyl 3,5-di(O-acetyl)-3',5'-diacetoxy-(DH.MB-530B-carboxylate)
549. Phenacyl 3,5-di(O-acetyl)-3',5'-diacetoxy-(DH.MB-530B-carboxylate)
550. 3,5-Di (O-butyryl)-3',5'-dibutyryloxy-(DH.MB-530B-carboxylic acid)
551. Sodium 3,5-di (O-butyryl)-3',5'-dibutyryloxy-(DH.MB-530B-carboxylate)
552. Methyl 3,5-di (O-butyryl)-3',5'-dibutyryloxy-(DH.MB-530B-carboxylate)
553. 3,5-Di(O-stearoyl)-3',5'-distearoyloxy-(DH.MB-530B-carboxylic acid)
554. Methyl 3,5-di(O-stearoyl)-3',5'-distearoyloxy-(DH.MB-530B-carboxylate)
555. 3,5-Di(O-linolenoyl)-3',5'-dilinolenoyloxy-(DH.MB-530B-carboxylic acid)
556. Sodium 3,5-di(O-linolenoyl)-3',5'-dilinolenoyloxy-(DH.MB-530B-carboxylate)
557. 3,5-Di(O-thienylacetyl)-3',5'-dithienylacetyl-(DH.MB-530B-carboxylic acid)
558. 3'-Oxo-5'-hydroxy-(DH.ML-236A-carboxylic acid)
559. Sodium 3'-oxo-5'-hydroxy-(DH.ML-236A-carboxylate)
560. Calcium bis[3'-oxo-5'-hydroxy-(DH.ML-236A-carboxylate)]
561. Aluminium tris[3'-oxo-5'-hydroxy-(DH.ML-236A-carboxylate)]
562. 3'-Oxo-5'-hydroxy-(DH.MB-530A-carboxylic acid)
563. Sodium 3'-oxo-5'-hydroxy-(DH.MB-530A-carboxylate)
564. Potassium 3'-oxo-5'-hydroxy-(DH.MB-530B-carboxylate)
565. 8'-(O-Acetyl)-3'-oxo-5'-hydroxy-(DH.ML-236A-carboxylic acid)
566. Sodium 8'-(O-acetyl)-3'-oxo-5'-hydroxy-(DH.ML-236A-carboxylate)
567. Methyl 8'-(O-acetyl)-3'-oxo-5'-hydroxy-(DH.ML-236A-carboxylate)
568. Ethyl 8'-(O-acetyl)-3'-oxo-5'-hydroxy-(DH.ML-236A-carboxylate)
569. 3'-Oxo-5'-hydroxy-(DH.ML-236B-carboxylic acid)
570. Sodium 3'-oxo-5'-hydroxy-(DH.ML-236A-carboxylate)
571. Potassium 3'-oxo-5'-hydroxy-(DH.ML-236B-carboxylate)
572. Calcium bis[3'-oxo-5'-hydroxy-(DH.ML-236B-carboxylate)]
573. Methyl 3'-oxo-5'-hydroxy-(DH.ML-236B-carboxylate)
574. Ethyl 3'-oxo-5'-hydroxy-(DH.ML-236B-carboxylate)
575. Phenacyl 3'-oxo-5'-hydroxy-(DH.ML-236B-carboxylate)
576. Pivaloyloxymethyl 3'-oxo-5'-hydroxy-(DH.ML-236B-carboxylate)
577. 8'-(O-Stearoyl)-3'-oxo-5'-hydroxy-(DH.ML-236A-carboxylic acid)
578. Sodium 8'-(O-stearoyl)-3'-oxo-5'-hydroxy-(DH.ML-236A-carboxylate)
579. Methyl 8'-(O-stearoyl)-3'-oxo-5'-hydroxy-(DH.ML-236A-carboxylate)
580. 8'-(O-Linolenoyl)-3'-oxo-5'-hydroxy-(DH.ML-236A-carboxylic acid)
581. Sodium 8'-(O-linolenoyl)-3'-oxo-5'-hydroxy-(DH.ML-236A-carboxylate)
582. Methyl 8'-(O-linolenoyl)-3'-oxo-5'-hydroxy-(DH.ML-236A-carboxylate)
583. 8'-(O-Benzoyl)-3'-oxo-5'-hydroxy-(DH.ML-236A -carboxylic acid)
584. Sodium 8'-(O-benzoyl)-3'-oxo-5'-hydroxy-(DH.ML-236A-carboxylate)
585. 8'-(O-Phenylacetyl)-3'-oxo-5'-hydroxy-(DH.ML-236A-carboxylic acid)
586. 8'-(O-2-Thienylacetyl)-3'-oxo-5'-hydroxy-(DH.ML-236A-carboxylic acid)
587. 3-(O-Acetyl)-3'-oxo-5'-hydroxy-(DH.ML-236A-carboxylic acid)
588. Sodium 3-(O-acetyl)-3'-oxo-5'-hydroxy-(DH.ML-236A-carboxylate)
589. Methyl 3-(O-acetyl)-3'-oxo-5'-hydroxy-(DH.ML-236A-carboxylate)
590. 3-(O-Acetyl)-3'-oxo-5'-hydroxy-(DH.ML-236B-carboxylic acid)
591. Sodium 3-(O-acetyl)-3'-oxo-5'-hydroxy-(DH.ML-236B-carboxylate)
592. Methyl 3-(O-acetyl)-3'-oxo-5'-hydroxy-(DH.ML-236B-carboxylate)
593. 3-(O-Benzoyl)-3'-oxo-5'-hydroxy-(DH.ML-236B-carboxylic acid)
594. Sodium 3-(O-benzoyl)-3'-oxo-5'-hydroxy-(DH.ML-236B-carboxylate)
595. Methyl 3-(O-benzoyl)-3'-oxo-5'-hydroxy-(DH.ML-236B-carboxylate)
596. 3,5,8'-Tri(O-acetyl)-5'-acetoxy-3'-oxo-(DH.ML-236A-carboxylic acid)
597. Sodium 3,5,8'-tri(O-acetyl)-5'-acetoxy-3'-oxo-(DH.ML-236A-carboxylate)
598. Methyl 3,5,8'-tri(O-acetyl)-5'-acetoxy-3'-oxo-(DH.ML-236A-carboxylate)
599. 3,5,8'-Tri(O-butyryl)-5'-butyryloxy-3'-oxo-(DH.ML-236A-carboxylic acid)
600. Sodium 3,5,8'-tri(O-butyryl)-5'-butyryloxy-3'-oxo-(DH.ML-236A-carboxylate)
601. Methyl 3,5,8'-tri(O-butyryl)-5'-butyryloxy-3'-oxo-(DH.ML-236A-carboxylate)

602. 3,5,8'-Tri(O-stearoyl)-5'-stearoyloxy-3'-oxo-(DH.ML-236A-carboxylic acid)
603. Sodium 3,5,8'-tri(O-stearoyl)-5'-stearoyloxy-3'-oxo-(DH.ML-236A-carboxylate)
604. Methyl 3,5,8'-tri(O-stearoyl)-5'-stearoyloxy-3'-oxo-(DH.ML-236A-carboxylate)
605. 3,5,8'-Tri(O-linolenoyl)-5'-linolenoyloxy-3'-oxo-(DH.ML-236A-carboxylic acid)
606. Sodium 3,5,8'-tri(O-linolenoyl)-5'-linolenoyloxy-3'-oxo-(DH.ML-236A-carboxylate)
607. Methyl 3,5,8'-tri(O-linolenoyl)-5'-linolenoyloxy-3'-oxo-(DH.ML-236A-carboxylate)
608. 3,5-Di(O-acetyl)-5'-acetoxy-3'-oxo-(DH.ML-236B-carboxylic acid)
609. Sodium 3,5-di(O-acetyl)-5'-acetoxy-3'-oxo-(DH.ML-236B-carboxylate)
610. Methyl 3,5-di(O-acetyl)-5'-acetoxy-3'-oxo-(DH.ML-236B-carboxylate)
611. 3,5-Di(O-propionyl)-5'-propionyloxy-3'-oxo-(DH.ML-236B-carboxylic acid)
612. Sodium 3,5-di(O-propionyl)-5'-propionyloxy-3'-oxo-(DH.ML-236B-carboxylate)
613. 3,5-Di(O-stearoyl)-5'-stearoyloxy-3'-oxo-(DH.ML-236B-carboxylic acid)
614. Sodium 3,5-di(O-stearoyl)-5'-stearoyloxy-3'-oxo-(DH.ML-236B-carboxylate)
615. Methyl 3,5-di(O-stearoyl)-5'-stearoyloxy-3'-oxo-(DH.ML-236B-carboxylate)
616. 3,5-Di(O-linolenoyl)-5'-linolenoyloxy-3'-oxo-(DH.ML-236B-carboxylic acid)
617. Sodium 3,5-di(O-linolenoyl)-5'-linolenoyloxy-3'-oxo-(DH.ML-236B-carboxylate)
618. Methyl 3,5-di(O-linolenoyl)-5'-linolenoyloxy-3'-oxo-(DH.ML-236B-carboxylate)
619. 3,5-Di(O-benzoyl)-5'-benzoyloxy-3'-oxo-(DH.ML-236B-carboxylic acid)
620. 3,5-Di(O-phenylacetyl)-5'-benzoyloxy-3'-oxo-(DH.ML-236B-carboxylic acid)
621. 3,5-Di(O-cyclohexanecarbonyl)-5'-cyclohexanecarbonyloxy-(DH.ML-236B-carboxylic acid)
622. 3,5-Di(O-2-thenoyl)-5'-(2-thenoyloxy)-3'-oxo-(DH.ML-236B-carboxylic acid)
623. 3,5-Di(O-2-thienylacetyl)-5'-(2-thienylacetyloxy)-3'-oxo-(DH.ML-236B-carboxylic acid)
624. 3,5-Di(O-phenylacetyl)-5'-phenylacetyloxy-3'-oxo-(DH.ML-236B-carboxylic acid)
625. 8'-(O-Acetyl)-3'-oxo-5'-hydroxy-(DH.MB-530A-carboxylic acid)
626. Sodium 8'-(O-acetyl)-3'-oxo-5'-hydroxy(DH.MB-530A-carboxylate)
627. Methyl 8'-(O-acetyl)-3'-oxo-5'-hydroxy-(DH.MB-530A-carboxylate)
628. Ethyl 8'-(O-acetyl)-3'-oxo-5'-hydroxy-(DH.MB-530A-carboxylate)
629. 3'-Oxo-5'-hydroxy-(DH.MB-530B-carboxylic acid)
630. Sodium 3'-oxo-5'-hydroxy-(DH.ML-236B-carboxylate)
631. Potassium 3'-oxo-5'-hydroxy-(DH.MB-530B-carboxylate)
632. Calcium bis[3'-oxo-5'-hydroxy(DH.MB-530B-carboxylate)]
633. Methyl 3'-oxo-5'-hydroxy-(DH.MB-530B-carboxylate)
634. Ethyl 3'-oxo-5'-hydroxy-(DH.MB-530B-carboxylate)
635. Phenacyl 3'-oxo-5'-hydroxy-(DH.MB-530B-carboxylate)
636. Pivaloyloxymethyl 3'-oxo-5'-hydroxy-(DH.MB-530B-carboxylate)
637. 8'-(O-Stearoyl)-3'-oxo-5'-hydroxy-(DH.MB-530A-carboxylic acid)
638. Sodium 8'-(O-stearoyl)-3'-oxo-5'-hydroxy-(DH.MB-530A-carboxylate)
639. Methyl 8'-(O-stearoyl)-3'-oxo-5'-hydroxy-(DH.MB-530A-carboxylate)
640. 8'-(O-Linolenoyl)-3'-oxo-5'-hydroxy-(DH.MB-530A-carboxylic acid)
641. Sodium 8'-(O-linolenoyl)-3'-oxo-5'-hydroxy-(DH.MB-530A-carboxylate)
642. Methyl 8'-(O-linolenoyl)-3'-oxo-5'-hydroxy-(DH.MB-530A-carboxylate)
643. 8'-(O-Benzoyl)-3'-oxo-5'-hydroxy-(DH.MB-530A-carboxylic acid)
644. Sodium 8'-(O-benzoyl)-3'-oxo-5'-hydroxy-(DH.MB-530A-carboxylate)
645. 8'-(O-Phenylacetyl)-3'-oxo-5'-hydroxy-(DH.MB-530A-carboxylic acid)
646. 8'-(O-2-Thienylacetyl)-3'-oxo-5'-hydroxy-(DH.MB-530A-carboxylic acid)
647. 3-(O-Acetyl)-3'-oxo-5'-hydroxy-(DH.MB-530A-carboxylic acid)
648. Sodium 3-(O-acetyl)-3'-oxo-5'-hydroxy-(DH.MB-530A-carboxylate)
649. Methyl 3-(O-acetyl)-3'-oxo-5'-hydroxy-(DH.MB-530A-carboxylate)
650. 3-(O-Acetyl)-3'-oxo-5'-hydroxy-(DH.MB-530B-carboxylic acid)
651. Sodium 3-(O-acetyl)-3'-oxo-5'-hydroxy-(DH.MB-530B-carboxylate)
652. Methyl 3-(O-acetyl)-3'-oxo-5'-hydroxy-(DH.MB-530B-carboxylate)
653. 3-(O-Benzoyl)-3'-oxo-5'-hydroxy-(DH.MB-530B-carboxylic acid)
654. Sodium 3-(O-benzoyl)-3'-oxo-5'-hydroxy-(DH.MB-530B-carboxylate)
655. Methyl 3-(O-benzoyl)-3'-oxo-5'-hydroxy-(DH.MB-530B-carboxylate)
656. 3,5,8'-Tri(O-acetyl)-5'-acetoxy-3'-oxo-(DH.MB-530A-carboxylic acid)
657. Sodium 3,5,8'-tri(O-acetyl)-5'-acetoxy-3'-oxo-(DH.MB-530A-carboxylate)
658. Methyl 3,5,8'-tri(O-acetyl)-5'-acetoxy-3'-oxo-(DH.MB-530A-carboxylate)
659. 3,5,8'-Tri(O-butyryl)-5'-butyryloxy-3'-oxo-(DH.MB-530A-carboxylic acid)
660. Sodium 3,5,8'-tri(O-butyryl)-5'-butyryloxy-3'-oxo-(DH.MB-530A-carboxylate)
661. Methyl 3,5,8'-tri(O-butyryl)-5'-butyryloxy-3'-oxo-(DH.MB-530A-carboxylate)
662. 3,5,8'-Tri(O-stearoyl)-5'-stearoyloxy-3'-oxo-(DH.MB-530A-carboxylic acid)
663. Sodium 3,5,8'-tri(O-stearoyl)-5'-stearoyloxy-3'-oxo-(DH.MB-530A-carboxylate)
664. Methyl 3,5,8'-tri(O-stearoyl)-5'-stearoyloxy-3'-oxo-(DH.MB-530A-carboxylate)
665. 3,5,8'-Tri(O-linolenoyl)-5'-linolenoyloxy-3'-oxo-(DH.MB-530A-carboxylic acid)
666. Sodium 3,5,8'-tri(O-linolenoyl)-5'-linolenoyloxy-3'-oxo-(DH.MB-530A-carboxylate)
667. Methyl 3,5,8'-tri(O-linolenoyl)-5'-linolenoyloxy-3'-oxo-(DH.MB-530A-carboxylate)
668. 3,5-Di(O-acetyl)-5'-acetoxy-3'-oxo-(DH.MB-530B-carboxylic acid)
669. Sodium 3,5-di(O-acetyl)-5'-acetoxy-3'-oxo-(DH.MB-530B-carboxylate)

670. Methyl 3,5-di(O-acetyl)-5'-acetoxy-3'-oxo-(DH.MB-530B-carboxylate)
671. 3,5-Di(O-propionyl)-5'-propionyloxy-3'-oxo-(DH.MB-530B-carboxylic acid)
672. Sodium 3,5-di(O-propionyl)-5'-propionyloxy-3'-oxo-(DH.MB-530B-carboxylate)
673. 3,5-(Di(O-stearoyl)-5'-stearoyloxy-3'-oxo-(DH.MB-530B-carboxylic acid)
674. Sodium 3,5-di(O-stearoyl)-5'-stearoyloxy-3'-oxo-(DH.MB-530B-carboxylate)
675. Methyl 3,5-di(O-stearoyl)-5'-stearoyloxy-3'-oxo-(DH.MB-530B-carboxylate)
676. 3,5-Di(O-linolenoyl)-5'-linolenoyloxy-3'-oxo-(DH.MB-530B-carboxylic acid)
677. Sodium 3,5-di(O-linolenoyl)-5'-linolenoyloxy-3'-oxo-(DH.MB-530B-carboxylate)
678. Methyl 3,5-di(O-linolenoyl)-5'-linolenoyloxy-3'-oxo-(DH.MB-530B-carboxylate)
679. 3,5-Di(O-benzoyl)-5'-benzoyloxy-3'-oxo-(DH.MB-530B-carboxylic acid)
680. 3,5-Di(O-phenylacetyl)-5'-benzoyloxy-3'-oxo-(DH.MB-530B-carboxylic acid)
681. 3,5-Di(O-cyclohexanecarbonyl)-5'-cyclohexanecarbonyloxy-(DH.MB-530B-carboxylic acid)
682. 3,5-Di(O-2-thenoyl)-5'-(2-thenoyloxy)-3'-oxo-(DH.MB-530B-carboxylic acid)
683. 3,5-Di(O-2-thienylacetyl)-5'-(2-thienylacetyloxy)-3'-oxo-(DH.MB-530B-carboxylic acid)
684. 3,5-Di(O-phenylacetyl)-5'-phenylacetyloxy-3'-oxo-(DH.MB-530B-carboxylic acid)
685. 3',5'-Dioxo-(DH.ML-236A-carboxylic acid)
686. Sodium 3',5'-dioxo-(DH.ML-236A-carboxylate)
687. Calcium bis[3',5'-dioxo-(DH.ML-236A-carboxylate)]
688. Methyl 3',5'-dioxo-(DH.ML-236A-carboxylate)
689. Ethyl 3',5'-dioxo-(DH.ML-236A-carboxylate)
690. 8'-(O-Acetyl)-3',5'-dioxo-(DH.ML-236A-carboxylic acid)
691. Sodium 8'-(O-acetyl)-3',5'-dioxo-(DH.ML-236A-carboxylate)
692. Methyl 8'-(O-acetyl)-3',5'-dioxo-(DH.ML-236A-carboxylate)
693. 8'-(O-propionyl)-3',5'-dioxo-(DH.ML-236A-carboxylic acid)
694. Sodium 8'-(O-propionyl)-3',5'-dioxo-(DH.ML-236A-carboxylate)
695. Methyl 8'-(O-propionyl)-3',5'-dioxo-(DH.ML-236A-carboxylate)
696. 3',5'-Dioxo-(DH.ML-236B-carboxylic acid)
697. Sodium 3',5'-dioxo-(DH.ML-236B-carboxylate)
698. Methyl 3',5'-dioxo-(DH.ML-236B-carboxylate)
699. Ethyl 3',5'-dioxo-(DH.ML-236B-carboxylate)
700. 8'-(O-Stearoyl)-3',5'-dioxo-(DH.ML-236A-carboxylic acid)
701. Sodium 8'-(O-stearoyl)-3',5'-dioxo-(DH.ML-236A-carboxylate)
702. Methyl 8'-(O-stearoyl)-3',5'-dioxo-(DH.ML-236A-carboxylate)
703. 8'-(O-Linolenoyl)-3',5'-dioxo-(DH.ML-236A-carboxylic acid)
704. Sodium 8'-(O-linolenoyl)-3',5'-dioxo-(DH.ML-236A-carboxylate)
705. 3-(O-Acetyl)-3',5'-dioxo-(DH.ML-236A-carboxylic acid)
706. Sodium 3-(O-acetyl)-3',5'-dioxo-(DH.ML-236A-carboxylate)
707. 3-(O-Acetyl)-3',5'-dioxo-(DH.ML-236B-carboxylic acid)
708. Sodium 3-(O-acetyl)-3',5'-dioxo-(DH.-ML-236B-carboxylate)
709. Methyl 3-(O-acetyl)-3',5'-dioxo-(DH.ML-236B-carboxylate)
710. 3,5-Di(O-acetyl)-3',5'-dioxo-(DH.ML-236B-carboxylic acid)
711. Sodium 3,5-di(O-acetyl)-3',5'-dioxo-(DH.ML-236B-carboxylate)
712. Methyl 3,5-di(O-acetyl)-3',5'-dioxo-(DH.ML-236B-carboxylate)
713. 3,5,8'-Tri(O-acetyl)-3',5'-dioxo-(DH.ML-236A-carboxylic acid)
714. Sodium 3,5,8'-tri(O-acetyl)-3',5'-dioxo-(DH.ML-236A-carboxylate)
715. 3',5'-Dioxo-(DH.MB-530A-carboxylic acid)
716. Sodium 3',5'-dioxo-(DH.MB-530A-carboxylate)
717. Calcium bis[3',5'-dioxo-(DH.MB-530A-carboxylate)]
718. Methyl 3',5'-dioxo-(DH.MB-530A-carboxylate)
719. Ethyl 3',5'-dioxo-(DH.MB-530A-carboxylate)
720. 8'-(O-Acetyl)-3',5'-dioxo-(DH.MB-530A-carboxylic acid)
721. Sodium 8'-(O-acetyl)-3',5'-dioxo-(DH.MB-530A-carboxylate)
722. Methyl 8'-(O-acetyl)-3',5'-dioxo-(DH.MB-530A-carboxylate)
723. 8'-(O-Propionyl)-3',5'-dioxo-(DH.MB-530A-carboxylic acid)
724. Sodium 8'-(O-propionyl)-3',5'-dioxo-(DH.MB-530A-carboxylate)
725. Methyl 8'-(O-propionyl)-3',5'-dioxo-(DH.MB-530A-carboxylate)
726. 3',5'-Dioxo-(DH.MB-530B-carboxylic acid)
727. Sodium 3',5'-dioxo-(DH.MB-530B-carboxylate)
728. Methyl 3',5'-dioxo-(DH.MB-530B-carboxylate)
729. Ethyl 3',5'-dioxo-(DH.MB-530B-carboxylate)
730. 8'-(O-Stearoyl)-3',5'-dioxo-(DH.MB-530A-carboxylic acid)
731. Sodium 8'-(O-stearoyl)-3',5'-dioxo-(DH.MB-530A-carboxylate)
732. Methyl 8'-(O-stearoyl)-3',5'-dioxo-(DH.MB-530A-carboxylate)
733. 8'-(O-Linolenoyl)-3',5'-dioxo-DH.MB-530A-carboxyic acid)
734. Sodium 8'-(O-linolenoyl)-3',5'-dioxo-(DH.MB-530A-carboxylate)
735. 3-(O-Acetyl)-3',5'-dioxo-(DH.MB-530A-carboxylic acid)
736. Sodium 3-(O-acetyl)-3',5'-dioxo-(DH.MB-530A-carboxylate)
737. 3-(O-Acetyl)-3',5'-dioxo-(DH.MB-530B-carboxylic acid)
738. Sodium 3-(O-acetyl)-3',5'-dioxo-(DH.MB-530B-carboxylate)
739. Methyl 3-(O-acetyl)-3',5'-dioxo-(DH.MB-530B-carboxylate)
740. 3,5-Di(O-acetyl)-3',5'-dioxo(DH.MB-530B-carboxylic acid)
741. Sodium 3,5-di(O-acetyl)-3',5'-dioxo(DH.MB-530B-carboxylate)
742. Methyl 3,5-di-(O-acetyl)-3',5'-dioxo(DH.MB-530B-carboxylate)
743. 3,5,8'-Tri(O-acetyl)-3',5'-dioxo-(DH.MB-530A-carboxylic acid)
744. Sodium 3,5,8'-tri(O-acetyl)-3',5'-dioxo-(DH.MB-530A-carboxylate)
745. 3',5'-Dioxo-(DH.ML-236B)
746. 3'-Acetoxy-5'-bromo-(DH.ML-236B)

747. 3'-(t-Butoxy)-5'-hydroxy-(DH.ML-236B)
748. Methyl 3'-bromo-5'-acetoxy-(DH.ML-236B-carboxylate)
749. Methyl 3'-acetoxy-5'-bromo-(DH.ML-236B-carboxyate)
750. 3'-Chloro-5'-hydroxy-(DH.ML-236B)
751. 3'-Methoxy-5'-hydroxy-(DH.ML-236B)
752. Methyl 3'-methoxy-5'-hydroxy-(DH.ML-236B-carboxylate)
753. 3'-Ethoxy-5'-hydroxy-(DH.ML-236B)
754. 3'-Butoxy-5'-hydroxy-(DH.ML-236B)
755. ML-236B 4'a,5'-epoxide
756. MB-530B 4'a,5'-epoxide Of the compounds listed above, the following are particularly preferred:

3',5'-Dihydroxy-(DH.ML-236B)
Methyl 3',5'-dihydroxy-(DH.ML-236B-carboxylate)
Sodium 3',5'-dihydroxy-(DH.ML-236B-carboxylate)
3-(O-Acetyl)-3',5'-diacetoxy-(DH.ML-236B)
3'-Oxo-5'-hydroxy-(DH.ML-236B)
3',5'-Dioxo-(DH.ML-236B)
3',5'-Dihydroxy-(TH.ML-236B)
3'-Acetoxy-5'-bromo-(DH.ML-236B)
3'-(t-Butoxy)-5'-hydroxy-DH.ML-236B)
Methyl 3'-bromo-5'-acetoxy-(DH.ML-236B-carboxylate)
Methyl 3'-acetoxy-5'-bromo-(DH.ML-236B-carboxylate)
3',5'-Dihydroxy-(DH.MB-530B)
Sodium 3',5'-dihydroxy-(DH.MB-530B-carboxylate)
Methyl 3',5'-dihydroxy-(DH.MB-530B-carboxylate)
3'-Chloro-5'-hydroxy-(DH.ML-236B)
3'-Methoxy-5'-hydroxy-(DH.ML-236B)
Methyl 3'-methoxy-5'-hydroxy-(DH.ML-236B-carboxylate)
3'-Ethoxy-5'-hydroxy-(DH.ML-236B)
3'-Butoxy-5'-hydroxy-(DH.ML-236B).

The compounds of the invention may be prepared by a variety of processes, all of which ultimately start from ML-236A, ML-236B, MB-530A, MB-530B, ML-236A carboxylic acid and MB-530A carboxylic acid, these all being preparable by cultivating appropriate microorganisms and isolating the chosen materials from the culture broth, as described in the prior art hereinbefore referred to and as specifically illustrated hereafter in the Preparations. The chemical structures of these compounds are as follows:

ML-236A

ML-236B

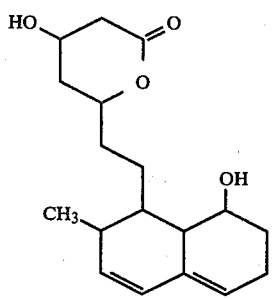

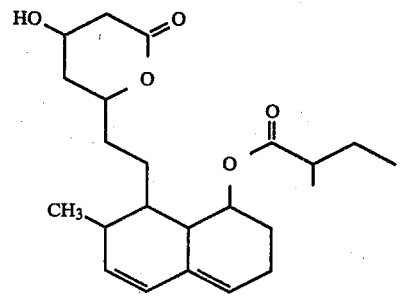

ML-530A

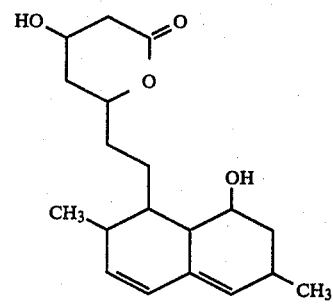

MB-530B

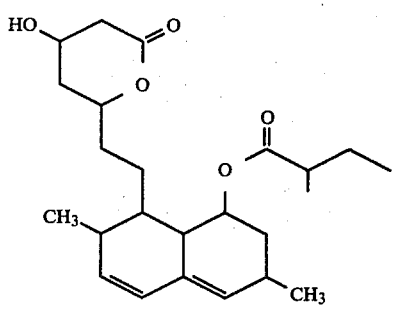

ML-236A carboxylic acid

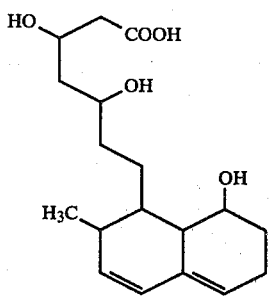

MB-530A carboxylic acid

-continued

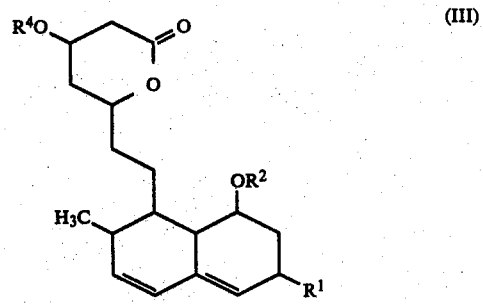

Preparation of the compounds of the invention may be effected by the following Methods or by a combination of them.

METHOD 1

Preparation of dihydro compounds by performic acid oxidation

Oxidation of compounds of formula (III):

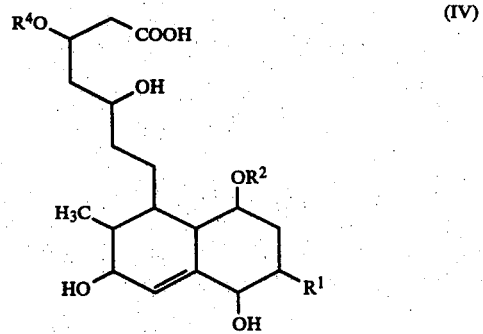
(III)

(in which $R^1$, $R^2$ and $R^4$ are as defined above) with performic acid gives a dihydro compound of formula (IV):

(IV)

(in which $R^1$, $R^2$ and $R^4$ are as defined above).

This reaction may be carried out in the same way as conventional performic acid oxidation reactions are carried out, for example simply by bringing the compound of formula (III) into contact with performic acid in a suitable solvent. Normally, the performic acid is formed in situ in the reaction system by adding hydrogen peroxide to formic acid. There is no particular limitation upon the nature of the solvent employed for this reaction, provided that it does not adversely affect the reaction and an excess of formic acid has been found to be a particularly convenient solvent to use, although other solvents may be employed, if desired. We prefer to use highly concentrated hydrogen peroxide, and, having regard to safety and ease of handling, a concentration of about 30% is convenient. The reaction is preferably conducted at room temperature or with cooling in order to suppress side reactions but the reaction can sometimes be accelerated by heating. The reaction time will depend upon the reaction temperature but normally from 1 to several hours is sufficient.

After completion of the oxidation, the desired compound of formula (IV) may be separated and purified by conventional methods from the reaction mixture. For example, one suitable recovery process comprises: concentrating the reaction mixture by evaporation under reduced pressure; dissolving the resulting residue in a suitable solvent, such as ethyl acetate; washing the solution with aqueous sodium sulphite and, if necessary, drying the solution; evaporating the solvent off under reduced pressure; adding an aqueous alkali, for example 0.1 N sodium hydroxide, and heating the mixture at 40° C. for 1 hour; cooling the mixture and then acidifying it; extracting the acidified mixture with a suitable solvent; and finally evaporating off the solvent to give the desired compound of formula (IV).

A similar oxidation reaction to that described above may be effected using a perbenzoic acid in place of the performic acid; reaction conditions are substantially the same as when performic acid is used as the oxidizing agent.

METHOD 2

Preparation of dihydro compounds by alkoxy-performic acid oxidation

Oxidation of a compound of formula (III):

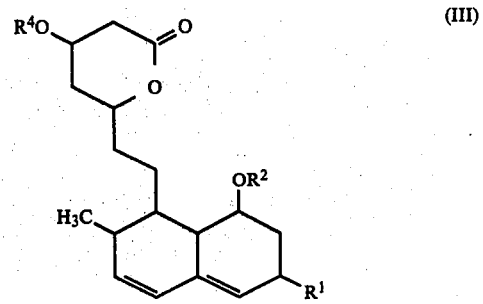
(III)

(in which $R^1$, $R^2$ and $R^4$ are as defined above) with an alkoxy-performic acid gives, as the principal product, a dihydro compound of formula (V):

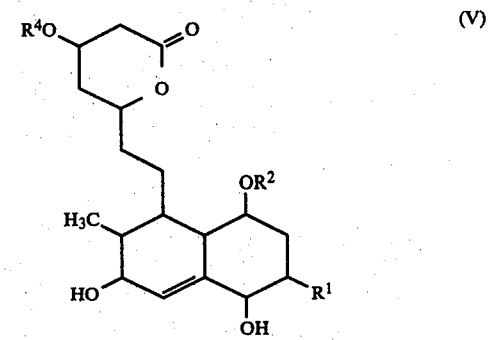
(V)

(in which $R^1$, $R^2$ and $R^4$ are as defined above), also formed in minor amounts are the corresponding 3'-oxo-5'-hydroxy compound of formula (VI):

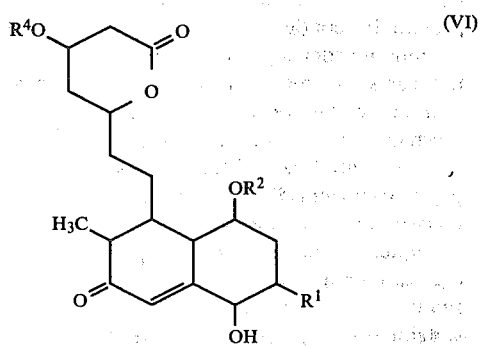

(VI)

(in which $R^1$, $R^2$ and $R^4$ are as defined above) and the corresponding 3'-perhydroxy-5'-hydroxy compound of formula (VII):

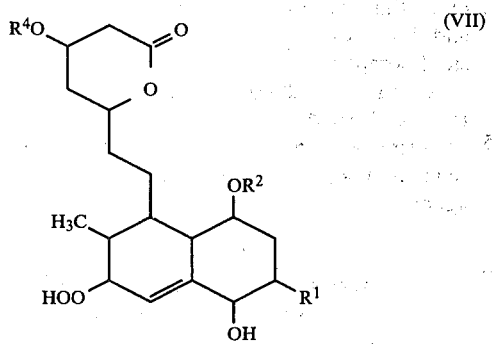

(VII)

(in which $R^1$, $R^2$ and $R^4$ are as defined above).

The conditions under which this reaction may be carried out are similar to those employed for conventional reactions of this type and the reaction may be effected simply by contacting the compound of formula (III) with an alkoxy-performic acid in a suitable solvent. There is no particular limitation on the nature of the solvent, provided that it has no adverse effect on the reaction and preferred solvents are such non-polar solvents as benzene, methylene chloride and carbon tetrachloride. The alkoxy-performic acid is preferably formed in situ in the reaction system by reacting an ester and hydrogen peroxide. The ester is preferably an ester of a carbonic acid and most preferably an ester of a chlorocarbonic acid. The hydrogen peroxide employed is preferably highly concentrated and, in view of safety and ease of handling, a concentration of about 30% is preferred. The reaction generally takes several hours. When the reaction is complete, the desired compounds may be separated from the reaction mixture by conventional methods, for example by separating the organic layer from the mixture, washing the organic layer with an aqueous solution of sodium sulphite and then evaporating off the solvent. The main product of formula (V) and the minor products of formulae (VI) and (VII) may be separated from each other by chromatography, preferably using silica gel.

METHOD 3

Preparation of a metal salt from the corresponding acid

Reaction of an acid of formula (VIII):

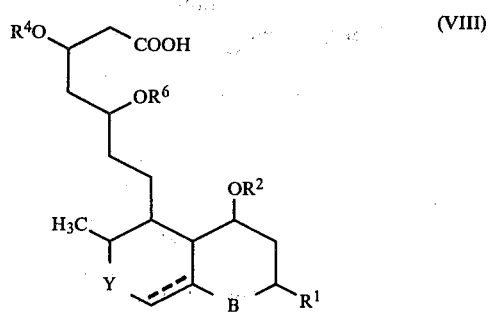

(VIII)

(in which $R^1$, $R^2$, $R^4$, $R^6$, B and the bond --- are as defined above; and Y represents a group of formula

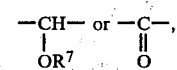

in which $R^7$ is as defined above) with a basic metal compound gives the corresponding metal carboxylate of formula (IX):

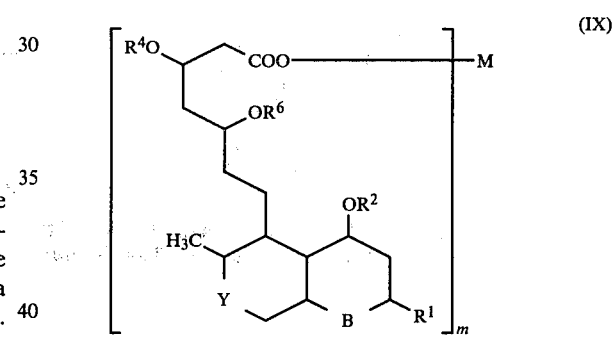

(IX)

(in which $R^1$, $R^2$, $R^4$, $R^6$, B, Y and the bond $\equiv\equiv\equiv$ are as defined above;

M represents a metal; and m represents the valency of the metal M).

This reaction may easily be carried out using techniques well-known for reacting acids and bases, for example by contacting the carboxylic acid of formula (VIII) with the basic metal compound in a suitable solvent. Examples of basic metal compounds which may be employed include oxides, hydroxides, bicarbonates and carbonates of the chosen metal M. The reaction will take place over a wide temperature range, but is most conveniently carried out at ambient temperature and will go rapidly to completion. When the reaction is complete, the desired product may be collected by conventional means, for example simply by evaporation of the solvent from the reaction mixture.

METHOD 4

Preparation of lactone from corresponding carboxylic acid

Acidification of a carboxylic acid of formula (X):

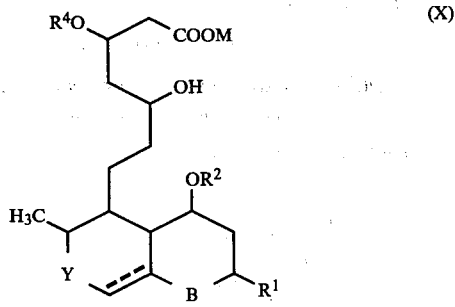

(X)

(in which $R^1$, $R^2$, $R^4$, B, Y and the bond ≡≡≡ are as defined above) results in ring-closure and the formation of the corresponding lactone of formula (XI):

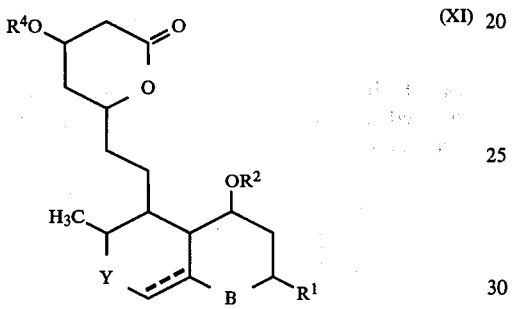

(XI)

(in which $R^1$, $R^2$, $R^4$, B, Y and the bond ≡≡≡ are as defined above).

This reaction may simply be carried out by contacting the carboxylic acid of formula (X) with an acid in the presence of a suitable solvent, as is well-known for the lactonization of δ-hydroxycarboxylic acids. There is no particular limitation on the nature of the solvent employed for this reaction, provided that it has no adverse effect upon the reaction, and we prefer to use such non-polar solvents as benzene and methylene chloride. A wide range of acids is available for use as the acid catalyst in this reaction, including: inorganic acids, such as hydrochloric acid or sulphuric acid; organic acids, such as formic acid, p-toluenesulphonic acid, trifluoroacetic acid and sulphonic acid-type ion-exchange resins; and Lewis acids, such as boron trifluoride and complexes thereof. Although the reaction is preferably conducted with heating, it will also proceed under other conditions. The time required for the reaction to go to completion will vary depending upon the reaction temperature, but it will generally take several hours. Once the reaction is over, the desired product may be collected by conventional means from the reaction mixture, for example by washing the reaction mixture with an aqueous alkali (such as sodium bicarbonate) to remove the acid catalyst, and then evaporating off the solvent.

METHOD 5

Preparation of a carboxylic acid ester by esterification of a metal carboxylate

Esterification of a metal carboxylate of formula (IX):

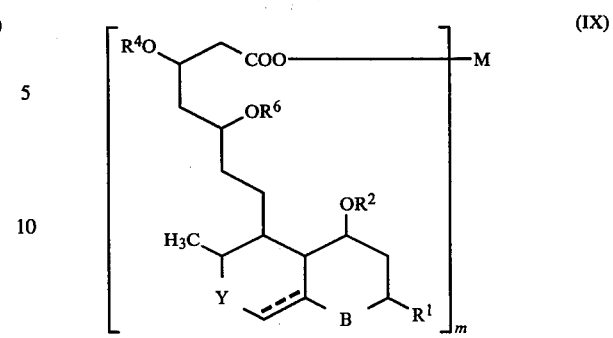

(IX)

(which may have been prepared as described in Method 4) with a suitable esterifying agent gives an ester of formula (XII):

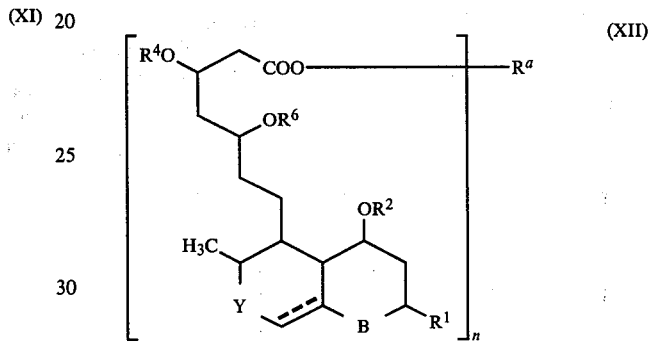

(XII)

(in which:

$R^1$, $R^2$, $R^4$, $R^6$, B, Y and the bond ≡≡≡ are as defined above;

$R^a$ represents the alcoholic moiety of an ester; and n is the valency of $R^a$).

The esterifying agent employed is preferably an compound of formula $R^aX_n$ (in which S represents a halogen atom, for example a chlorine or bromine atom). The nature of the group represented by $R^a$ will depend upon the ester which it is desired to produce, but it is preferably an alkyl, aralkyl or phenacyl group, any of which may be unsubstituted or have one or more substituents.

The reaction may be conducted under conditions well-known for the esterification of metal carboxylates, for example by contacting the metal carboxylate (IX) with the esterifying agent in a suitable inert solvent. There is no particular limitation upon the nature of the solvent to be employed in this reaction, provided that it has no adverse effect upon the reaction and suitable solvents include dimethylformamide, dimethyl sulphoxide, tetrahydrofuran, hexamethylphosphoramide, acetone or methyl ethyl ketone. The reaction may be conducted over a wide range of temperatures, but it is preferably effected at ambient temperature or with heating, in most cases preferably at ambient temperature. The time required for the reaction will vary, depending upon the reaction temperature, but the reaction will generally require from 1 to 20 hours. When the reaction is complete, the desired product may be collected by conventional means, for example it can be extracted from the reaction mixture with water and a water-immiscible solvent and then obtained from the resulting solution by evaporation of the solvent.

METHOD 6

Preparation of carboxylic acid esters by cleavage of a lactone

Solvolysis of a lactone of formula (XI):

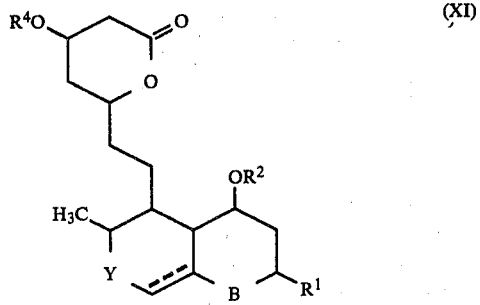

(in which $R^1$, $R^2$, $R^4$, B, Y and the bond --- are as defined above) in the presence of a suitable organic hydroxy compound will yield an ester of formula (XIII):

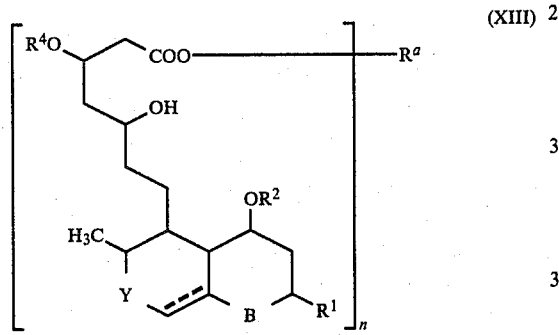

(in which $R^1$, $R^2$, $R^4$, B, Y, $R^a$, n and the bond $\equiv$ are as defined above).

The organic hydroxy group compound employed is a compound of formula $R^a(OH)_n$ and, in this case, $R^a$ is an ester group capable of formation by solvolysis of a lactone and is preferably an alkyl or a substituted alkyl group.

The reaction may be effected simply by contacting the compound (XI) with the hydroxy compound, preferably an alcohol, in the presence of an acid catalyst, which may be an inorganic acid (e.g. hydrochloric acid or sulphuric acid), a Lewis acid (e.g. boron trifluoride) or an acidic ion-exchange resin. In some cases, the reaction may be effected in the presence of a solvent, the nature of which is not critical, provided that it has no adverse effect upon the reaction. Suitable solvents are such organic solvents as benzene, diethyl ether and chloroform. If the alcohol or other hydroxy compound is a liquid, then this is preferably used as the solvent. The reaction is preferably conducted with heating, for example at a temperature from 50° C. to the boiling point of the reaction mixture and the reaction will generally require several hours. After completion of the reaction, the desired compound may be collected from the reaction mixture by conventional means. For example, if the catalyst employed is an ion-exchange resin, the desired compound may be obtained by filtering off the catalyst and then evaporating the solvent from the filtrate. On the other hand, if the catalyst is an inorganic acid or a Lewis acid, the reaction mixture is first neutralized and then extracted with the suitable solvent, after which the solvent is evaporated off to give the desired compound.

METHOD 7

Preparation of carboxylic acid esters by esterification with a diazo compound

Reaction of a carboxylic acid of formula (VIII):

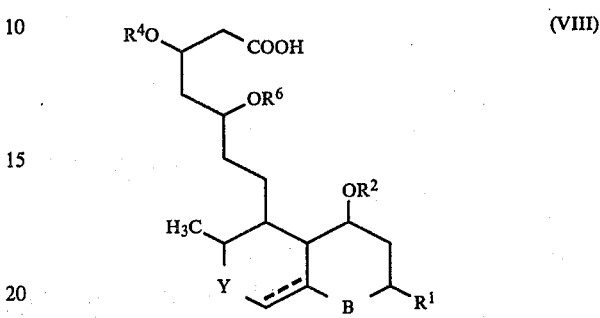

(in which $R^1$, $R^2$, $R^4$, $R^6$, B, Y and the bond $\equiv$ are as defined above) with a diazo compound gives an ester of formula (XIV):

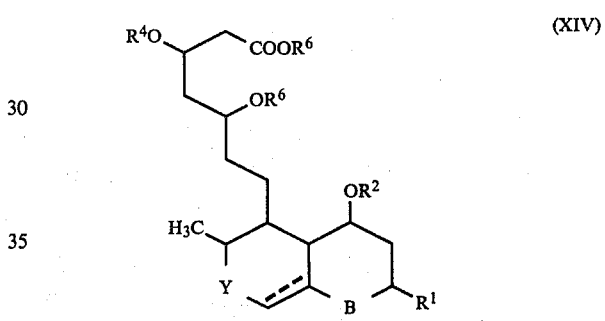

(in which $R^1$, $R^2$, $R^4$, $R^6$, B, Y and the bond $\equiv$ are as defined above) and $R^b$ represents an alkyl or substituted alkyl group capable of formation by a diazo compound, preferably a lower alkyl group or a benzhydryl group.

This reaction can readily be accomplished by conventional methods, for example by contacting the carboxylic acid (VIII) with a diazo compound, such as diazomethane or diphenyldiazomethane, in a suitable solvent. There is no particular limitation on the nature of the solvent to be employed in this reaction, provided that it has no adverse effect upon the reaction. Suitable solvents, which are preferably organic, include diethyl ether, tetrahydrofuran and methylene chloride. The reaction is preferably carried out with cooling, in order to suppress side reactions, but it may also be effected at room temperature. The reaction will generally require from 1 to 20 hours. After completion of the reaction, the desired compound may be collected from the reaction mixture by conventional means, for example by evaporating off the solvent and then subjecting the product to chromatography.

METHOD 8

Preparation of acyl derivatives from corresponding hydroxy compounds

Compounds of formula (I) in which one or more of $R^2$, $R^3$, $R^4$, $R^6$ and $R^7$ represents a hydrogen atom may be acylated by conventional methods for the acylation of aliphatic hydroxy groups, preferably by either of the following processes:

(A) Acylation using a reactive derivative of an acid

In this process, the hydroxy group-containing compound is contacted with a reactive derivative of the acid having the desired acyl group, for example an acid halide (such as an acid chloride or acid bromide), an acid anhydride, a mixed acid anhydride (for example a mixed acid anhydride of an acid with a chlorocarbonic acid ester) or a sulphonic acid chloride. The reaction is preferably carried out in the presence of a solvent and also preferably in the presence of a base. There is no particular limitation on the nature of the solvent to be employed, provided that it has no adverse effect upon the reaction and suitable solvents, which are preferably organic, include chloroform, methylene chloride, diethyl ether, tetrahydrofuran and dioxane. Preferred bases include such organic amines as pyridine, 4-(N,N-dimethylamino)pyridine, quinoline, triethylamine, N-methylmorpholine, N-methylpiperidine and N,N-dimethylaniline. Where the amine employed is a liquid at the reaction temperature, for example pyridine, it may also serve as the solvent. The reaction is preferably carried out at room temperature or with cooling in order to control side reactions, but it will also proceed at elevated temperatures. The reaction time will depend upon the reaction temperature and upon the nature of the reagents, but the reaction will normally be complete within a period of from 10 minutes to 10 hours. After completion of the reaction, the desired product may be recovered by conventional means, for example by diluting the reaction mixture with ice-water, extracting the mixture with a water-immiscible solvent and distilling the solvent from the extract.

(B) Acylation with a condensing agent

This reaction may be carried out under conventional conditions employing a free acid corresponding to the acyl group which it is desired to introduce, in the presence of a condensing agent and, in this case, the compound of formula (I) containing a free hydroxy group is simply contacted with the acid in the presence of the condensing agent. The condensing agent is preferably a dehydrating agent, for example a carbodiimide, such as dicyclohexylcarbodiimide. The reaction is normally carried out in the presence of a solvent, the nature of which is not critical, provided that it has no adverse effect upon the reaction. Suitable solvents include dimethylformamide, dimethylacetamide, acetonitrile, pyridine, methylene chloride, chloroform and dioxane. The reaction may be carried out over a wide temperature range, but, in order to control side reactions, we normally prefer to conduct it at room temperature or with cooling; however, the reaction will also proceed at elevated temperatures. The time required for the reaction will vary depending upon the reaction temperature and the reagents employed, but the reaction will normally be complete within a period of from 1 to 20 hours. The desired compound may then be recovered from the reaction mixture by conventional means, for example by filtering off insolubles, diluting the filtrate with water, extracting the resulting mixture with a water-immiscible solvent and then distilling the solvent from the extract to give the desired product.

In the case of both of the above acylation reactions, where the starting material contains two or more free hydroxy groups, any of the mono, di, tri, tetra or pentaacyl derivatives can be obtained by controlling the amount of acylating agent employed. If a mixture of these compounds is obtained, the separate compounds may be isolated using conventional isolation techniques, for example chromatography on silica gel.

METHOD 9

Preparation of 3'-oxo compounds from 3'-hydroxy compounds

Oxidation of a 3'-hydroxy compound of formula (XV):

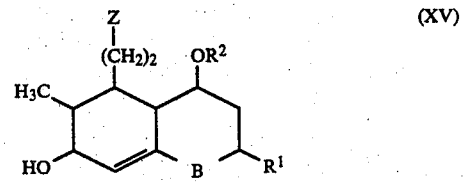

(in which $R^1$, $R^2$, B and Z are as defined above) gives the corresponding 3'-oxo compound of formula (XVI):

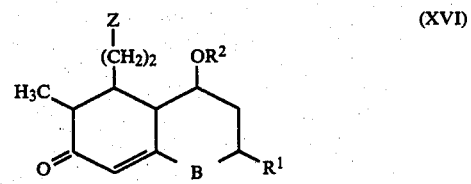

(in which $R^1$, $R^2$, B and Z are as defined above).

The oxidizing agent employed for this reaction may be any such agent capable of converting a hydroxy group to an oxo group without affecting the remainder of the molecule. The preferred oxidizing agent is manganese dioxide. The reaction can easily be accomplished by contacting the 3'-hydroxy compound of formula (XV) with freshly prepared manganese dioxide in a suitable solvent. It is preferred to use an excess, for example from 5 to 15 times the stoichiometric amount, of manganese dioxide. There is no particular limitation on the nature of the solvent to be used in this reaction, provided that it has no adverse effect upon the reaction. Aprotic solvents, such as methylene chloride and chloroform, are preferred. The reaction is normally and preferably carried out at ambient temperature, although it will even proceed with cooling or heating. The progress of the reaction can be followed by thin layer chromatography and it will normally take 1 or more days to go to completion. When the reaction is over, the desired compound of formula (XVI) can be recovered from the reaction mixture by conventional means, for example by filtering off insolubles and then evaporating the solvent from the filtrate to give the desired compound.

Where a compound of formula (XV) in which B represents a group of formula —CH(OH)— is exployed, the oxidation will normally convert this hydroxy group to an oxo group, thus giving the 3',5'-dioxo compound.

METHOD 10

Preparation of 3',5'-dioxo compound from 3',5'-dihydroxy compound

Reaction of a dihydroxy compound of formula (XVII):

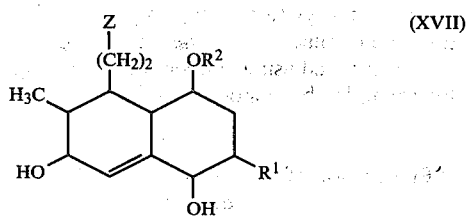

(in which $R^1$, $R^2$ and Z are as defined above) with a strong oxidizing agent gives the corresponding dioxo compound of formula (XVIII):

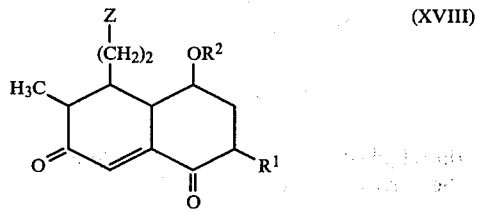

(in which $R^1$, $R^2$ and Z are as defined above).

The oxidizing agent employed for this reaction is preferably chromic acid or a chromic acid compound or complex, such as pyridinium chlorochromate. The reaction can easily be carried out in the same way as conventional chromic acid oxidization reactions, for example by contacting the dihydroxy compound of formula (XVII) with the oxidizing agent in the presence of a suitable solvent. There is no particular limitation upon the nature of the solvent, provided that it does not adversely affect the reaction. The solvent employed is preferably an aprotic solvent, such as methylene chloride. The reaction is normally and preferably conducted at room temperature, but it will also proceed with cooling or heating. The reaction will normally require several hours to complete. After completion of the reaction, the desired dioxo compound of formula (XVIII) can be recovered from the reaction mixture by conventional means, for example by filtering off insolubles and then evaporating the solvent from the filtrate to give the desired compound.

METHOD 11

Preparation of tetrahydro compound

Catalytic reduction of a dihydro compound of formula (XIX):

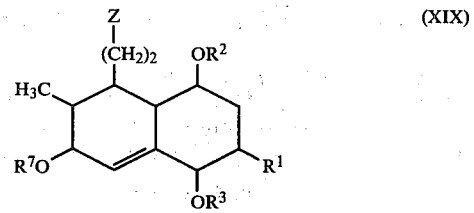

(in which $R^1$, $R^2$, $R^3$, $R^7$ and Z are as defined above) gives the corresponding tetrahydro compound of formula (XX):

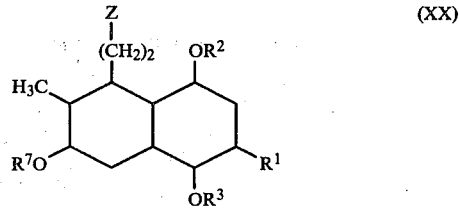

(in which $R^1$, $R^2$, $R^3$, $R^7$ and Z are as defined above).

This reaction may be carried out using conditions conventional for catalytic reduction reactions, for example by contacting the dihydro compound of formula (XIX) with hydrogen in a suitable solvent and in the presence of a catalyst. Any conventional reduction catalyst may be employed, for example: a platinum catalyst, such as platinum oxide, platinum black or platinum-silk; a palladium catalyst, such as palladium black, palladium-on-carbon, palladium-barium sulphate or palladium silk; a rhodium catalyst, or a nickel catalyst. Palladium-on-carbon is particularly suitable. There is no particular limitation upon the nature of solvent employed in this reaction, provided that it has no adverse effect on the reaction. The solvent is preferably one in which the starting material and product have a high solubility, for example an alcohol (such as methanol or ethanol), acetic acid or a mixture of one or more of these solvents with another solvent, such as diethyl ether. The reaction will take place over a wide temperature range, but it is preferably conducted at ambient temperature. The progress of the reaction can be detected by the amount of hydrogen absorbed and the reaction will generally require several hours. After completion of the reaction, the desired compound may be recovered from the reaction mixture by conventional means, for example by filtering off insolubles and then evaporating the solvent from the filtrate to leave the desired compound.

METHOD 12

Preparation of a 3'-hydroxy compound from a 3'-perhydroxy compound

Decomposition of the perhydroxy group at the 3'-position of a compound of formula (XXI):

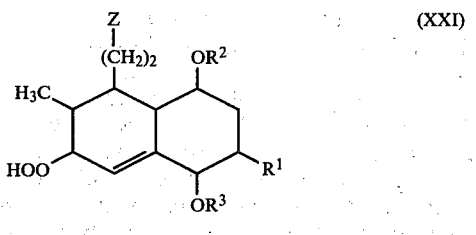

(in which $R^1$, $R^2$, $R^3$ and Z are as defined above) gives the corresponding 3'-hydroxy compound of formula (XXII):

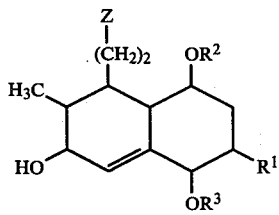

(in which $R^1$, $R^2$, $R^3$ and Z are as defined above).

This decomposition is catalyzed by a base and so the reaction may be carried out simply by contacting the perhydroxy compound of formula (XXI) with a base in a suitable solvent. There is no particular limitation upon the nature of the solvent to be employed for this reaction, provided that it has no adverse effect upon the reaction. The preferred solvent is water or a solvent readily soluble in water, such as an aqueous alcohol. The base used as catalyst in this reaction is preferably an aqueous solution of a basic alkali metal compound (particularly a metal hydroxide, such as sodium hydroxide or potassium hydroxide). The reaction is preferably carried out with heating, for example at a temperature of 40°–50° C., but the reaction will also proceed under other conditions. The reaction will normally take from 1 to 2 hours to go to completion. After completion of the reaction, the desired 3'-hydroxy compound may be recovered from the reaction mixture by conventional means, for example by neutralizing the mixture with a mineral acid, extracting the product with a suitable solvent and then evaporating the solvent from the extract to give the desired compound.

METHOD 13

Preparation of 3'-halo compound from 3'-hydroxy compound

Halogenation of a 3'-hydroxy compound of formula (XXII):

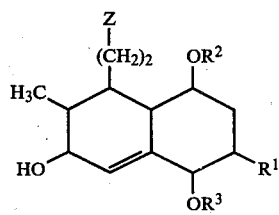

(in which $R^1$, $R^2$, $R^3$ and Z are as defined above) gives the corresponding 3'-halo compound of formula (XXIII):

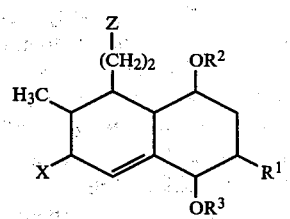

(in which $R^1$, $R^2$, $R^3$, Z and X are as defined above).

This reaction may be accomplished simply by contacting the 3'-hydroxy compound of formula (XXII) with an acid HX in a suitable solvent. The nature of the solvent to be employed in this reaction is not particularly critical, provided that it does not adversely affect the reaction. An organic solvent, such as acetonitrile, is preferably employed. The reaction temperature may vary over a wide range but is preferably around ambient temperature. The time required for the reaction, which will vary depending upon the reaction temperature, is usually several hours. After completion of the reaction, the desired product may be recovered from the reaction mixture by conventional means, for example by neutralizing the mixture with an aqueous alkaline solution, removing the solvent by distillation, adding water to the residue, extracting the resulting solution with a suitable solvent and then distilling the solvent from the extract to give the desired product.

METHOD 14

Preparation of epoxide

Oxidation of a compound of formula (III):

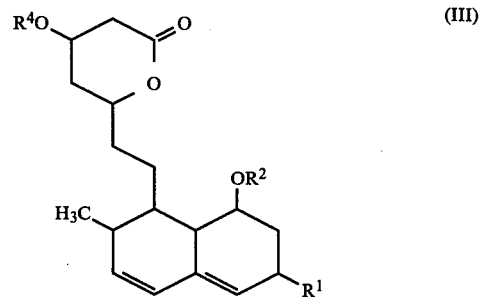

(in which $R^1$, $R^2$ and $R^4$ are as defined above) can yield an epoxide of formula (II):

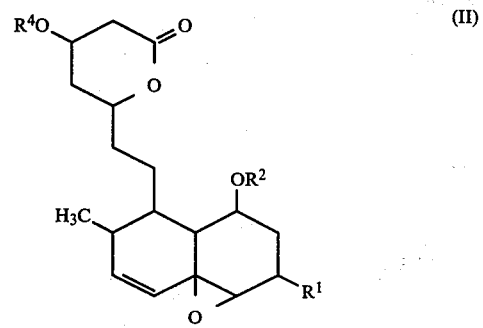

(in which $R^1$, $R^2$ and $R^4$ are as defined above).

The oxidization may be effected by means of a peracid, such as perbenzoic acid or perchlorobenzoic acid or an ester of a peracid, for example an ester of perchloroformic acid, in the presence of a suitable solvent. There is no particular limitation upon the nature of the solvent to be employed in this reaction, provided that it does not adversely affect the reaction. Suitable solvents include methylene chloride, chloroform and ethyl acetate. The peracid or peracid ester is preferably formed in situ.

One particularly preferred method of carrying out this reaction is to add ethyl chloroformate, disodium phosphate and hydrogen peroxide to a solution of the compound (III) in a suitable organic solvent. The reaction is preferably effected at ambient temperature or below and the time required for the reaction is usually about 1 hour. After completion of the reaction, the desired product may be separated from the reaction mixture by conventional means, for example as follows: the organic phase is separated from the reaction mixture, the excess hydrogen peroxide is decomposed with an aqueous solution of sodium sulphite; the mixture is washed with water and, if necessary, dried; and then the solvent is distilled off to give the epoxide (II).

METHOD 15

Preparation of 3'-alkoxy compound by alcoholysis of epoxide

A 3'-alkoxy compound of formula (XXIV):

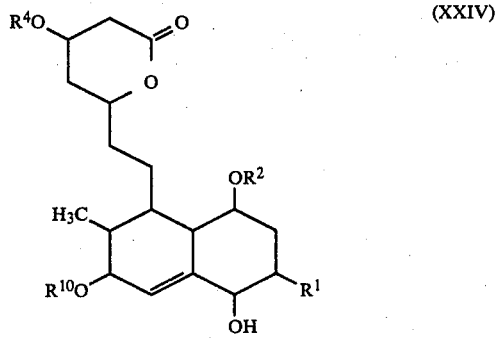

(in which $R^1$, $R^2$ and $R^4$ are as defined above and $R^{10}$ represents an alkyl group) may be prepared by alcoholysis of an epoxide of formula (II), prepared as described in Method 14. This alcoholysis reaction may be effected simply by reacting the epoxide with an alcohol in the presence or absence of a solvent by conventional means, as is well-known in the art.

METHOD 16

Preparation of 3'-acyloxy-5'-halo compound

A 3'-acyloxy-5'-halo compound of formula (XXV):

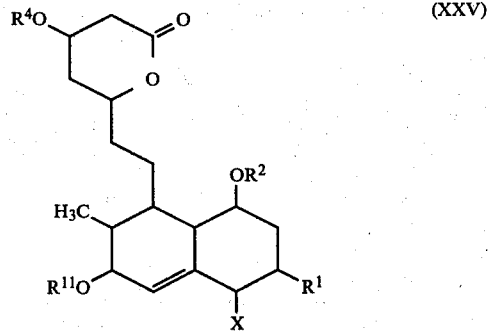

(in which $R^1$, $R^2$, $R^4$ and X are as defined above and $R^{11}$ represents an acyl group) may be prepared by reacting a compound of formula (III):

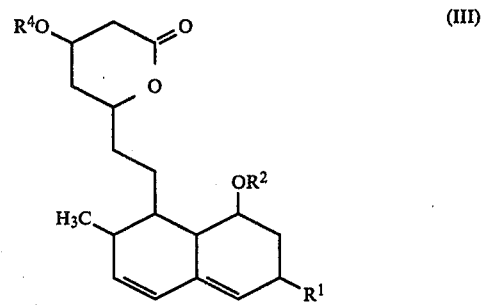

(in which $R^1$, $R^3$ and $R^4$ are as defined above) with a halogenating agent and a carboxylic acid corresponding to the acyloxy group which it is desired to introduce.

The reaction is preferably effected in the presence of a solvent, which is preferably the carboxylic acid participating in the reaction, provided that this carboxylic acid is liquid at the reaction temperature and is a solvent for the reagents. The halogenating agent employed may be any such agent capable of releasing a halide ion, for example N-bromosuccinimide, N-chlorosuccinimide, N-bromoacetamide or N-bromophthalimide. The reaction is preferably effected at ambient temperature and will normally require several hours. After completion of the reaction, the desired product may be recovered from the reaction mixture by conventional means, for example by diluting the mixture with water, extracting the mixture with a suitable organic solvent and then subjecting the resulting organic solution to column chromatography.

The above Methods may be combined in any suitable order to prepare any of the compounds of formula (I).

The compounds of the invention have been found to inhibit the activity of 3-hydroxy-3-methylglutaryl coenzyme A reductase, which is the rate- determining enzyme in the biosynthesis of cholesterol. According to the method of Knauss et al [J. Biol. Chem., 234, 2835 (1959)], the inhibitory activities of the compounds of the invention against the biosynthesis of cholesterol, expressed as their $ID_{50}$ values (i.e. the concentration required to inhibit the biosynthesis of cholesterol by 50%), varied from 1.0 to 0.03 μg/ml. Moreover, the compounds of the invention have been found to have a particularly low toxicity, as compared with the compounds of the prior art described hereinabove. Thus, for example, mice have been found to survive when 3',5'-dihydroxy-(DH.ML-236B) is administered intraperitoneally in doses as high as 1000 μg/kg body weight.

The compounds of the invention may be administered for the treatment of hypercholesteraemia or the prevention of arteriosclerosis by any conventional means, but they are preferably administered in the form of tablets or capsules. The daily dose will vary depending upon the age, body weight and condition of the patient but in general the compounds of the invention are preferably administered in an amount of from 1 mg to 10 mg per day, for adults, in a single dose or in divided doses.

The preparation of the compounds of the invention is further illustrated by the following Examples. Preparation of certain of the starting materials used in these Examples is illustrated by the Preparations.

PREPARATION 1

Preparation of MB-530A 300 liters of a culture medium having a pH of 5.5 before sterilization and containing 5% w/v glucose, 0.5% w/v corn steep liquor, 2% w/v peptone (Kyokuto brand, available from Kyokuto Seiyaku KK, Japan) and 0.5% ammonium chloride were charged into a 600 liter fermenter and inoculated with a culture of *Monascus ruber* SANK 15177 (FERM 4956, NRRL 12081). Cultivation of the microorganism was continued for 120 hours at 27° C. with an aeration rate of 300 liters/minute and agitation at 190 revolutions per minute.

At the end of this time, the culture broth was filtered in a filter press to give a filtrate and a filter cake comprising wet cells of the microorganism.

Figure 2:
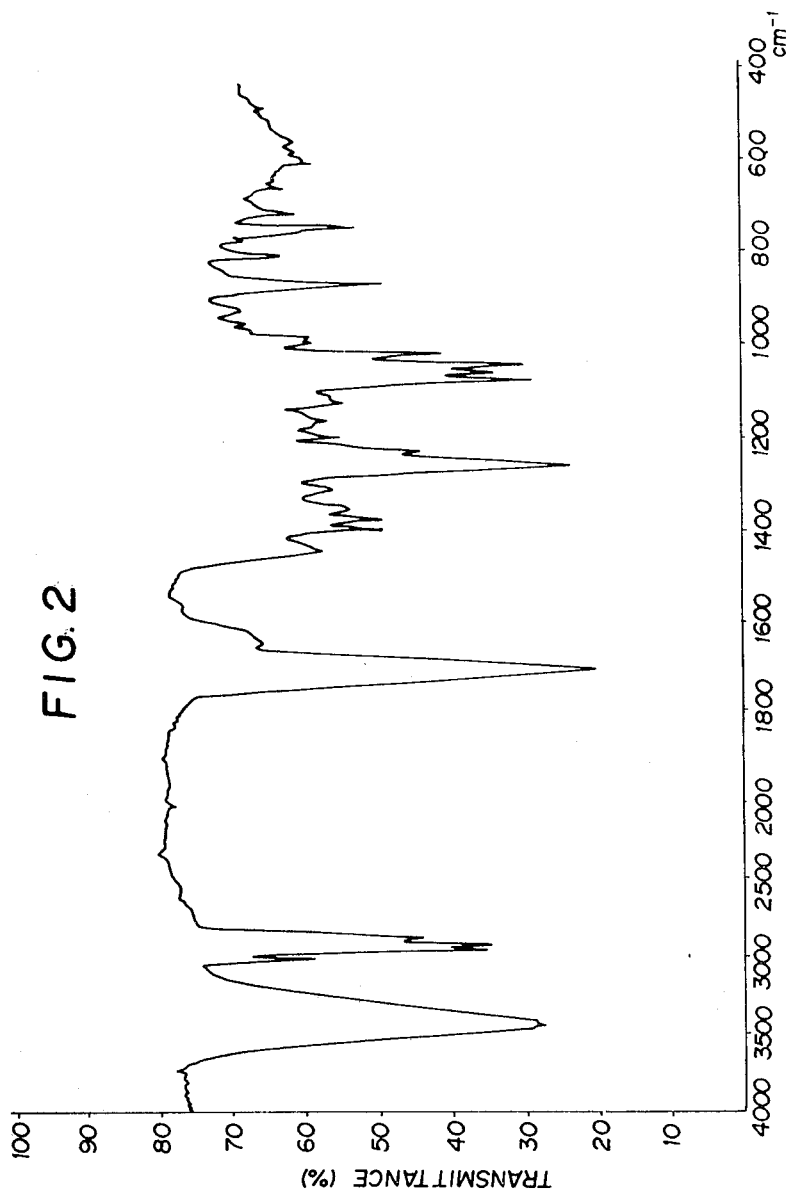
Figure 3:
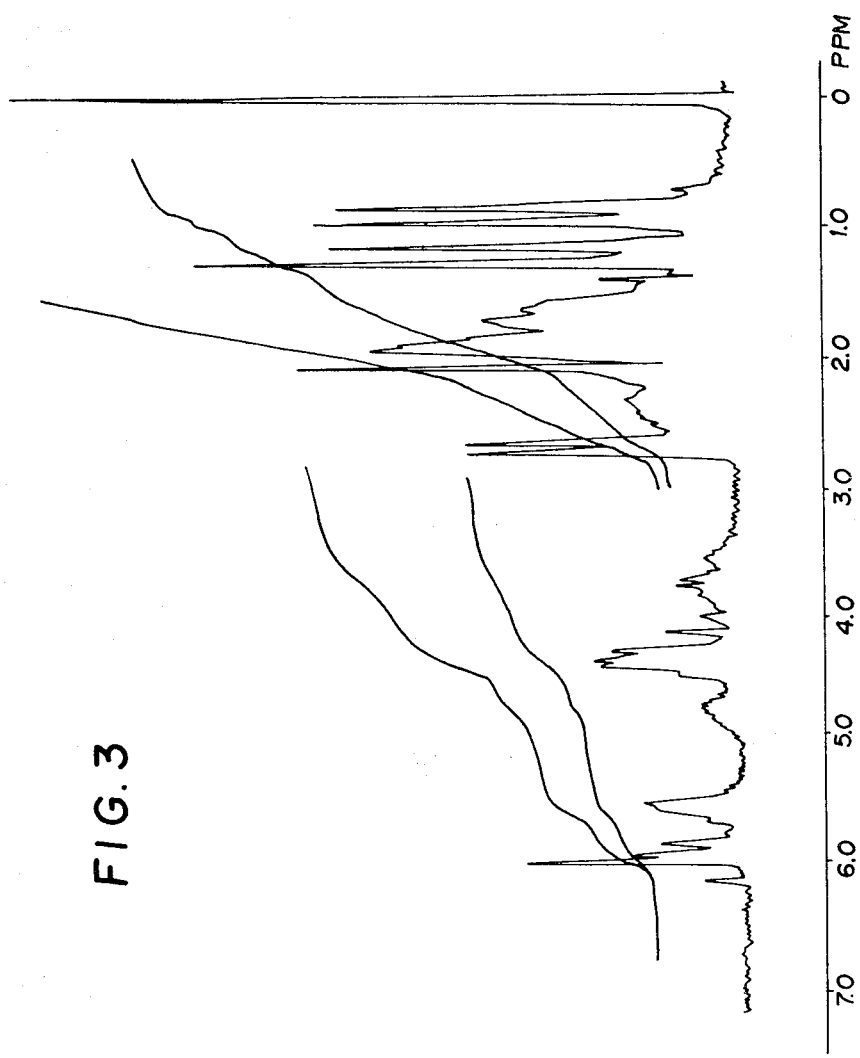

The filtrate was adjusted to a pH of 3.0 by the addition of 6 N hydrochloric acid and then extracted with 400 liters of ethyl acetate. The extract (about 400 liters) was concentrated by evaporation under reduced pressure and then dehydrated over anhydrous sodium sulphate, after which it was evaporated to dryness, to give about 60 g of an oily product. This oily product was washed with ethylcyclohexane and with hexane and the residue (20 g) was evaporated by chromatography using a liquid chromatography device for large volume sampling (System 500 liquid chromatography, produced by Waters Co., U.S.A.), eluted with 60% v/v aqueous methanol. Fractions having a chromatographic retention time of 6 minutes were collected and concentrated by evaporation under reduced pressure to give 100 mg of the desired MB-530A as an oily product. This oily MB-530A was recrystallized from a mixture of acetone and diethyl ether to give 57 mg of the desired product in the form of colourless needles having the following properties:

1. Melting Point: 92°–93° C.
2. Elemental Analysis: Calculated for $C_{19}H_{28}O_4$: C, 69.76%; H, 8.68%. Found: C, 71.22%; H, 8.81%.
3. Molecular weight: 320 (by mass analysis).
4. Molecular formula: $C_{19}H_{28}O_4$.
5. Ultraviolet Absorption Spectrum: As shown in FIG. 1 of the accompanying drawings.
6. Infrared Absorption Spectrum: As shown in FIG. 2 of the accompanying drawings.
7. Nuclear Magnetic Resonance Spectrum: As shown in FIG. 3 of the accompanying drawings.
8. Solubility: readily soluble in methanol, ethanol, acetone, ethyl acetate, chloroform and carbon tetrachloride, soluble in benzene; insoluble in hexane and petroleum ether.
9. Colouration reaction: a pink colour is seen when a thin layer chromatogram on silica gel of the compound is developed with 50% v/v sulphuric acid.
10. Inhibitory activity against the biosynthesis of cholesterol: a 50% inhibition of the synthesis of cholesterol in a rat liver is observed at a concentration of 0.04 µg/ml.

PREPARATION 2

3-(O-Butyryl)-(ML-236A)

918 mg of ML-236A were dissolved in 5 ml of pyridine, and 1 ml of butyric anhydride was added dropwise to the resulting solution. The mixture was then left to stand at room temperature overnight, after which water was added and then the mixture was extracted with diethyl ether. The extract was washed, in turn, with water, with a saturated aqueous solution of sodium bicarbonate, with a 1 N aqueous solution of hydrochloric acid and again with water, after which it was dried over anhydrous sodium sulphate. The solvent was then evaporated off and the residue was subjected to chromatography through silica gel eluted with a 5:1 by volume mixture of benzene and ethyl acetate to give 930 mg of the desired product as a colourless oil.

Elemental Analysis: Calculated for $C_{22}H_{32}O_5$: C, 70.21%; H, 8.51%. Found: C, 69.96%; H, 8.69%.

Nuclear Magnetic Resonance Spectrum (CDCl$_3$) δ ppm: 0.95 (3H, triplet); 4.27 (1H, multiplet); 5.32 (multiplet).

Infrared Absorption Spectrum (liquid film) $\nu_{max}$ cm$^{-1}$: 3460, 1740.

PREPARATION 3

3,8'-Di(O-butyryl)-ML-236A)

306 mg of ML-236A and 0.5 ml of pyridine were dissolved in 3 ml of methylene chloride, and 0.5 ml of butyryl chloride was added, with ice-cooling, to the resulting solution. The mixture was then stirred at room temperature for 1 hour, after which it was washed with water and the organic phase was separated and dried over anhydrous sodium sulphate. The solvent was then evaporated from the organic phase and the residue was subjected to column chromatography through silica gel eluted with a 10:1 by volume mixture of benzene and ethyl acetate, to give 384 mg of the desired compound as a colourless oil.

Elemental Analysis: Calculated for $C_{26}H_{38}O_6$: C, 69.96%; H, 8.52%. Found: C, 70.14%; H, 8.31%.

Nuclear Magnetic Resonance Spectrum (CDCl$_3$) δ ppm: 0.93 (6H, triplet); 5.2–5.5 (2H, multiplet).

Infrared Absorption Spectrum (liquid film) $\nu_{max}$ cm$^{-1}$: 1735, 1250, 1175.

PREPARATION 4

8'-(O-Butyryl)-(ML-236A)

918 mg of ML-236A and 0.36 ml of pyridine were dissolved in 10 ml of methylene chloride. The resulting solution was cooled with ice and then 0.35 ml of butyryl chloride was added dropwise. After stirring the mixture for 1 hour, water was added and then the organic phase was separated and washed with water, after which it was dried over anhydrous sodium sulphate. The solvent was then evaporated from this organic phase and the residue was subjected to column chromatography through silica gel. The column was first eluted with a 10:1 by volume mixture of benzene and ethyl acetate, which gave the 3,8'-diacyl compound (see Preparation 3). The column was then eluted with a 5:1 by volume mixture of benzene and ethyl acetate, giving the 3-acyl compound (see Preparation 2). Finally, the column was eluted with a 2:1 by volume mixture of benzene and ethyl acetate, giving 395 mg of the desired compound in the form of colourless crystals melting at 124°–125° C.

Elemental Analysis: Calculated for $C_{22}H_{32}O_5$: C, 70.21%; H, 8.51%. Found: C, 70.25%; H, 8.50%.

Nuclear Magnetic Resonance Spectrum (CDCl$_3$) δ ppm: 0.95 (3H, triplet); 4.42 (1H, multiplet).

Infrared Absorption Spectrum (Nujol-Trade Mark) $\nu_{max}$ cm$^{-1}$: 3400, 1730, 1710.

By following the procedures described in the above Preparations 2–4, it is possible to obtain other acyl derivatives of ML-236A, ML-236B, MB-530A and MB-530B.

EXAMPLE 1

3′,5′-Dihydroxy-(DH.ML-236B)

(a) 10 g of ML-236B were dissolved, with heating, in 50 ml of formic acid and then the solution was cooled to 10° C. Whilst stirring the solution at 10° C., 3.5 g of 30% aqueous hydrogen peroxide were added dropwise. After completion of this addition, the mixture was stirred for a further 60 minutes and then concentrated by evaporation under reduced pressure. The residue was dissolved in 200 ml of ethyl acetate and the resulting solution was washed with a 0.2 M aqueous solution of sodium sulphite. The solvent was then evaporated from the solution under reduced pressure. To the residue were added 200 ml of a 0.1 N aqueous solution of sodium hydroxide, and then the mixture was heated, with stirring, to 40° C. After complete dissolution, the solution was cooled and its pH was adjusted to a value of 2.5 by the addition of 6 N hydrochloric acid. The solution was then extracted with ethyl acetate and the extract was washed with a saturated aqueous solution of sodium chloride and then dried over anhydrous sodium sulphate. The solvent was then evaporated from the extract, giving 9.5 g of 3′,5′-dihydroxy-(DH.ML-236B-carboxylic acid) as an oil.

(b) The carboxylic acid prepared in step (a) above was dissolved in a small amount of ethyl acetate and then 100 ml of benzene and a small amount of trifluoroacetic acid were added to the resulting solution, and this mixture was heated under reflux for 30 minutes. After cooling the mixture, it was washed, in turn, with a 5% w/v aqueous solution of sodium bicarbonate and with a saturated aqueous solution of sodium chloride; it was then dried over anhydrous sodium sulphate. Evaporation of the solvent from this solution under reduced pressure gave 5 g of the title compound as a crude oily product. This product was then subjected to chromatography through silica gel to give 2.5 g of the title product as a pure colourless powder melting at 63°–67° C.

Optical rotation $[\alpha]_D^{20}$: +42.7° (c=1.03, methanol).

Mass analysis (M+): 424 ($C_{23}H_{36}O_7$).

Ultraviolet Absorption Spectrum (methanol): terminal absorption only.

Infrared Absorption Spectrum (KBr) $\nu_{max}$ cm$^{-1}$: 3300, 1720.

Nuclear Magnetic Resonance Spectrum (CDCl$_3$) δ ppm: 3.9 (1H, double doublet, J=3 and 5 Hz); 4.3 (2H, multiplet); 5.3 (1H, multiplet); 5.9 (1H, double doublet, J=1.5 and 5 Hz).

Thin layer chromatography (silica gel, Merck Co. 5717, eluted with ethyl acetate): $R_f$=0.17.

Liquid chromatography (μ-Bondapack-C18, 20% v/v aqueous acetonitrile): R time=11 minutes.

EXAMPLE 2

Methyl 3′,5′-dihydroxy-(DH.ML-236B-carboxylate)

890 mg of 3′,5′-dihydroxy-(DH.ML-236B-carboxylic acid), prepared as described in step (a) of Example 1, were cooled to 5° C. and then dissolved in 1 ml of anhydrous methanol. A solution of diazomethane in diethyl ether was added little by little to the resulting solution. After consumption of the diazomethane had ceased, a slight excess of the diazomethane solution was added and the mixture was then left to stand for 5 minutes, at the end of which time the solvent was evaporated off.

The residue, which consisted of 900 mg of the title compound in a crude state, was dissolved in ethyl acetate and then purified by chromatography through silica gel to give 600 mg of the pure compound as an oil.

Optical rotation $[\alpha]_D^{20}$: +35° (c=1.02, methanol).

Mass analysis (M+): 456.

Elemental Analysis: Calculated for $C_{24}H_{40}O_8$: C, 60.53%; H, 8.77%. Found: C, 61.02%; H, 8.90%.

Ultraviolet Absorption Spectrum (methanol): terminal absorption only.

Infrared Absorption Spectrum (liquid film) $\nu_{max}$ cm$^{-1}$: 3300, 1720.

Nuclear Magnetic Resonance Spectrum (CDCl$_3$) δ ppm: 2.6 (2H, doublet); 3.6 (3H, singlet); 3.8–4.2 (3H, multiplet); 5.3 (1H, multiplet); 5.9 (1H, double doublet, J=1.5 and 5 Hz).

EXAMPLE 3

Sodium 3′,5′-dihydroxy-(DH.ML-236B-carboxylate)

To 1.52 g of 3′,5′-dihydroxy-(DH.ML-236B) were added 36 ml of a 0.1 N aqueous solution of sodium hydroxide. The mixture was stirred at 50° C. for 2 hours and then the resulting solution was cooled and freeze-dried to give 1.6 g of the title compound as a colourless powder.

Elemental Analysis: Calculated for $C_{23}H_{37}O_8Na$: C, 59.48%; H, 7.97%; Na, 4.96%. Found: C, 58.98%; H, 8.12%; Na, 5.11%.

Infrared Absorption Spectrum (KBr) $\nu_{max}$ cm$^{-1}$: 1720–1710.

EXAMPLE 4

3-(O-Acetyl)-3′,5′-diacetoxy-(DH.ML-236B)

500 mg of 3′,5′-dihydroxy-(DH.ML-236B) were dissolved in 1 ml of dry pyridine, and then the solution was mixed with 0.5 ml of acetic anhydride and left to stand for 2 hours. The mixture was then poured into 50 ml of ice-water and stirred, after which it was extracted with ethyl acetate. The extract was washed, in turn, with dilute aqueous hydrochloric acid and with a saturated aqueous solution of sodium chloride, after which it was dried over anhydrous sodium sulphate. The solvent was then evaporated from the extract and the residue was purified by column chromatography through silica gel to give 380 mg of the title compound as an oil.

Elemental Analysis: Calculated for $C_{29}H_{42}O_{10}$: C, 63.27%; H, 7.64%. Found: C, 63.02%; H, 7.60%.

Infrared Absorption Spectrum (liquid film) $\nu_{max}$ cm$^{-1}$: 1730, 1720.

Nuclear Magnetic Resonance Spectrum (CDCl$_3$) δ ppm: 2.0 (1H, double doublet, J=1.5 and 5 Hz); 4.8 (3H, multiplet); 5.3 (1H, multiplet); 5.8 (9H, singlet).

EXAMPLE 5

3′-Oxo-5′-hydroxy-(DH.ML-236B)

150 mg of 3′,5′-dihydroxy-(OH.ML-236B) were dissolved in 5 ml of methylene chloride, and then 1.5 g of freshly prepared manganese dioxide were added to the solution. The mixture was stirred slowly at room temperature for 6 days. At the end of this time, the reaction mixture was filtered using a Celite (Trade Mark) filter aid, and then the filtrate was concentrated by evaporation under reduced pressure. The resulting concentrate was then subjected to column chromatography through silica gel eluted first with methylene chloride and then with a 80:20 by volume mixture of methylene chloride and acetone as eluent, it was then further purified by passing through a Lobar column (produced by Merck Co., S-60) eluted with 95:5 by volume mixture of ethyl acetate and acetone, giving 65 mg of the title compound as an oil.

Mass analysis (M+): 422.

Elemental Analysis: Calculated for $C_{23}H_{34}O_7$: C, 65.36%; H, 8.12%. Found: C, 65.29%; H, 7.88%.

Infrared Absorption Spectrum (Nujol) $\nu_{max}$ cm$^{-1}$: 3300, 1720, 1690.

Nuclear Magnetic Resonance Spectrum (CDCl$_3$) δ ppm: 2.7 (1H, multiplet); 4.2 (2H, multiplet); 4.5 (1H, multiplet); 5.2 (1H, multiplet); 5.8 (1H, doublet, J=1.5 Hz).

Ultraviolet Absorption Spectrum (methanol) $\nu_{max}$ nm: 233 (ε9700).

EXAMPLE 6

3′,5′-Dioxo-(DH.Ml-236B)

300 mg of 3′,5′-dihydroxy-(DH.ML-236B) were dissolved in 10 ml of methylene chloride, and 400 mg of pyridinium chlorochromate were added to the resulting solution. The mixture was stirred at room temperature for 3 hours, after which it was mixed with 50 ml of ethyl acetate and stirred until homogeneous; it was then filtered. The solvent was evaporated under reduced pressure from the filtrate and the residue was chromatographed through a silica gel column eluted first with benzene and then with ethyl acetate; it was then further purified through a Lobar column eluted with a 90:10 by volume mixture of ethyl acetate and acetone, to give 85 mg of the title compound in the form of an oil.

Mass analysis (M+): 420.

Elemental Analysis: Calculated for $C_{23}H_{32}O_7$: C, 65.67%; H, 7.68%. Found: C, 65.21%; H, 7.30%.

Ultraviolet Absorption Spectrum (methanol) $\nu_{max}$ nm: 240 (ε6300).

Nuclear Magnetic Resonance Spectrum (CDCl$_3$) δ ppm: 4.4 (1H, multiplet); 4.7 (1H, multiplet); 5.6 (1H, broad singlet); 6.6 (1H, doublet, J=3 Hz).

Infrared Absorption Spectrum (Nujol) $\nu_{max}$ cm$^{-1}$: 3300, 1710, 1680.

EXAMPLE 7

3′,5′-Dihydroxy-(TH.ML-236B)

300 mg of 3′,5′-dihydroxy-(DH.ML-236B) were dissolved in 30 ml of ethanol and then 30 mg of 5% w/w palladium-on-carbon were added to the resulting solution. The mixture was shaken at room temperature in a hydrogen atmosphere until absorption of hydrogen ceased. The mixture was then filtered and the filtrate was evaporated to remove the solvent, giving 270 mg of the title compound in the form of an oil.

Mass analysis (M+): 426.

Elemental Analysis: Calculated for $C_{23}H_{38}O_7$: C, 64.74%; H, 8.99%. Found: C, 64.55%; H, 8.90%.

Infrared Absorption Spectrum (Nujol) $\nu_{max}$ cm$^{-1}$: 3300, 1710.

Nuclear Magnetic Resonance Spectrum (CDCl$_3$) δ ppm: 3.8 (1H, multiplet); 4.2 (2H, multiplet); 4.7 (1H, multiplet); 5.3 (1H, broad singlet).

EXAMPLE 8

3′-Acetoxy-5′-bromo-(DH.ML-236B)

A solution of 390 mg of ML-236B in 4 ml of acetic acid was cooled with ice-water, and then 150 mg of N-bromoacetamide was added all at once to the solution. The temperature of the mixture was allowed to gradually rise to room temperature, and then the mixture was stirred at that temperature for 4 hours. Water was then added to the reaction mixture, after which it was extracted with ethyl acetate. The solvent was then evaporated from the extract to give an oil, which was purified by chromatography through a Lobar column using as eluent a 2:1 by volume mixture of benzene and ethyl acetate. 381 mg of the desired compound were obtained in the form of an oil.

Infrared Absorption Spectrum (liquid film) $\nu_{max}$ cm$^{-1}$: 3450, 1740, 1730, 1720, 1240.

Nuclear Magnetic Resonance Spectrum (CDCl$_3$) δ ppm: 1.98 (3H, singlet); 4.28 (1H, multiplet); 4.5–5.0 (2H, multiplet).

Elemental Analysis: Calculated for $C_{25}H_{37}BrO_7$: C, 56.71%; h, 6.99%; Br, 15.12%. Found: C, 56.90%; H, 6.89%; Br, 15.24%.

EXAMPLE 9

Methyl 3′-acetoxy-5′-bromo-(DH.ML-236B-carboxylate)

To a solution of 935 mg of 3′-acetoxy-5′-bromo-(DH.ML-236B) in 10 ml of methanol were added 15 mg of anhydrous potassium carbonate, and the resulting mixture was then stirred at room temperature for 1 hour. At the end of this time, the mixture was concentrated to one-half of its original volume by evaporation under reduced pressure. 50 ml of benzene were added to the residue and the resulting mixture was washed twice with water and then with a saturated aqueous solution of sodium chloride; it was then dried over anhydrous sodium sulphate. The solvent was then distilled off under reduced pressure and the residue was purified by column chromatography through silica gel using as eluent a 90:10 by volume mixture of ethyl acetate and hexane. There were obtained 747 mg of the title compound.

Mass analysis (M+): 561.

Infrared Absorption Spectrum (liquid film) $\nu_{max}$ cm$^{-1}$: 3450, 1720.

Nuclear Magnetic Resonance Spectrum (CDCl$_3$) δ ppm: 2.00 (3H, singlet); 3.70 (3H, singlet); 4.8–5.1 (2H, multiplet); 5.4 (1H, multiplet); 5.95 (1H, broad doublet, J=6 Hz).

EXAMPLE 10

3′-Chloro-5′-hydroxy-(DH.ML-236B)

To 450 mg of 3′,5′-dihydroxy-(DH.ML-236B) were added 10 ml of acetonitrile and 0.2 ml of concentrated hydrochloric acid, and the mixture was then allowed to react at room temperature for 2 hours. At the end of this time, the mixture was neutralized by the addition of a 1 N aqueous solution of sodium hydroxide, and the acetonitrile was distilled off under reduced pressure. To the residue were added 50 ml of distilled water and the resulting mixture was extracted with ethyl acetate. The extract was washed with 50 ml of a saturated aqueous solution of sodium chloride, dried over anhydrous sodium sulphate and then concentrated to dryness to give 400 mg of an oily substance. This substance was purified by column chromatography through silica gel (Lobar column) using as eluent a 3:2 by volume mixture of ethyl acetate and benzene. There were obtained 300 mg of the desired product as an oily substance.

Elemental Analysis:

Calculated for $C_{23}H_{35}O_6Cl$: C, 62.44%; H, 7.92%; Cl, 7.92%. Found: C, 62.21%; H, 7.75%; Cl, 7.72%.

Mass analysis (M+): 442.

Infrared Absorption Spectrum (chloroform) $v_{max}$ cm$^{-1}$: 3300, 1720.

Nuclear Magnetic Resonance Spectrum (CDCl$_3$) $\delta$ ppm: 4.2 (3H, multiplet); 4.6 (1H, multiplet); 5.2 (1H, multiplet); 5.8 (1H, double doublet, J=1.5 and 5 Hz).

EXAMPLE 11

3'-Methoxy-5'-hydroxy-(DH.ML-236B)

To a solution of 2.4 g of ML-236B in 10 ml of methylene chloride were added 1.0 g of ethyl chloroformate, 1.6 g of disodium phosphate and 10 ml of 35% hydrogen peroxide, whilst maintaining the temperature of the mixture at 20° C. The mixture was then allowed to react, under vigorous stirring, for 1 hour, after which the mixture was allowed to stand and the supernatant was discarded. 200 ml of ethyl acetate were added to the residue and the resulting mixture was washed twice, each time with 100 ml of a 5% w/v aqueous solution of sodium sulphite, and once with a saturated aqueous solution of sodium chloride; it was then dried over anhydrous sodium sulphate and the solvent was distilled off under reduced pressure. The residue was recrystallized from a mixture of diethyl ether and petroleum ether, to afford 1.5 g of a crystalline intermediate melting at 115° C. To this intermediate were added 10 ml of methanol, and the mixture was allowed to react at room temperature for 30 minutes to give the desired product quantitatively.

Mass analysis (M+): 438.

Elemental Analysis: Calculated for $C_{24}H_{38}O_7$: C, 65.75%; H, 8.68%. Found: C, 65.84%; H, 8.75%.

Infrared Absorption Spectrum (KBr) $v_{max}$ cm$^{-1}$: 3300, 1720.

Nuclear Magnetic Resonance Spectrum (CDCl$_3$) $\delta$ ppm: 2.5 (2H, multiplet).

EXAMPLE 12

Methyl 3'-methoxy-5'-hydroxy-(DH.ML-236B-carboxylate)

To 1 g of the crystalline intermediate referred to and prepared as described in Example 11 were added 20 ml of methanol, and the mixture was allowed to react at room temperature for 2 hours to afford the desired product quantitatively. The product was purified by recrystallization from a mixture of diethyl ether and petroleum ether, to give the pure product melting at 111° C.

Mass analysis (M+): 470.

Elemental Analysis: Calculated for $C_{25}H_{42}O_8$: C, 63.83%; H, 8.94%. Found: C, 64.13%; H, 9.00%.

Infrared Absorption Spectrum (KBr) $v_{max}$ cm$^{-1}$: 3400, 1740, 1725.

Nuclear Magnetic Resonance Spectrum (CDCl$_3$) $\delta$ ppm: 2.4 (2H, doublet); 3.2 (3H, singlet); 3.6 (3H, singlet); 5.3 (1H, multiplet); 5.8 (1H, doublet).

EXAMPLE 13

3'-Ethoxy-5'-hydroxy-(DH.ML-236B)

To 1 g of the crystalline intermediate referred to and prepared as described in Example 11 were added 20 ml of ethanol and a catalytic amount of trifluoroacetic acid and the mixture was allowed to react at room temperature for 2 hours to afford the desired product quantitatively.

Mass analysis (M+): 452.

Elemental Analysis: Calculated for $C_{25}H_{40}O_7$: C, 66.37%; H, 8.85%. Found: C, 66.21%; H, 8.93%.

Infrared Absorption Spectrum (liquid film) $v_{max}$ cm$^{-1}$: 3450, 1730, 1260.

Nuclear Magnetic Resonance Spectrum (CDCl$_3$) $\delta$ ppm: 2.5 (2H, doublet); 3.5 (2H, multiplet); 4.3 (2H, multiplet); 4.6 (1H, multiplet); 5.3 (1H, multiplet); 5.8 (1H, multiplet).

EXAMPLE 14

3'-Butoxy-5'-hydroxy-(DH.ML-236B)

To 1 g of the crystalline intermediate referred to in and prepared as described in Example 11 were added 20 ml of butanol and a catalytic amount of p-toluenesulphonic acid, and the resulting mixture was refluxed for 30 minutes. After cooling, the reaction mixture was washed, in turn, with a 5% w/v aqueous solution of sodium bicarbonate and with a saturated aqueous solution of sodium chloride; it was then dried over anhydrous sodium sulphate and the solvent was distilled off under reduced pressure to give the desired product quantitatively.

Mass analysis (M+): 480.

Elemental Analysis: Calculated for $C_{27}H_{44}O_7$: C, 67.50%; H, 9.17%. Found: C, 66.81%; H, 9.01%.

Infrared Absorption Spectrum (liquid film) $v_{max}$ cm$^{-1}$: 3450, 1723, 1260.

EXAMPLE 15

ML-236B 4'a,5'-Epoxide

To a solution of 2.4 g of ML-236B in 10 ml of methylene chloride were added 1.6 g of ethyl chloroformate and 1.6 g of disodium phosphate, and then 10 ml of 35% hydrogen peroxide were added to the resulting mixture. The mixture was allowed to react, with vigorous stirring, for 1 hour, after which it was allowed to stand and the supernatant was discarded. To the residue were added 200 ml of ethyl acetate, and the resulting mixture was washed twice with 100 ml of a 5% w/v aqueous solution of sodium sulphite and then once with 100 ml of a saturated aqueous solution of sodium chloride. The mixture was then dried over anhydrous sodium sulphate and the solvent was distilled off. The residue was recrystallized from a mixture of diethyl ether and petroleum ether to give 1.5 g of the desired product in the form of crystals melting at 117°–118° C.

Mass analysis (M+): 406.

Elemental Analysis: Calculated for $C_{23}H_{34}O_6$: C, 67.98%; H, 8.37%. Found: C, 68.05%; H, 8.35%.

Infrared Absorption Spectrum (KBr) $v_{max}$ cm$^{-1}$: 3440, 1740, 1725.

Nuclear Magnetic Resonance Spectrum (CDCl$_3$) $\delta$ ppm: 3.1 (1H, singlet); 4.3 (1H, multiplet); 4.6 (1H, multiplet); 5.0 (1H, doublet); 5.1 (1H, multiplet); 6.2 (2H, multiplet).

EXAMPLE 16

3',5'-Dihydroxy(DH.MB-530B)

To a solution of 400 mg of MB-530B in 40 ml of ethyl acetate were added 330 mg of m-chloroperbenzoic acid, and the resulting mixture was stirred at room temperature for 1 hour. The reaction mixture was then washed with a 5% w/v aqueous solution of sodium sulphite and then with a saturated aqueous solution of sodium chloride, after which it was dried over anhydrous sodium sulphate. The solvent was then evaporated off to give 39 mg of the corresponding epoxide. This epoxide was reacted in 5 ml of acetone with 2 ml of water at room temperature for 2 hours and then purified through a Lobar column ( RP-8, eluted with a 1:1 by volume mixture of methanol and water) to give 300 mg of the desired compound as an oily substance.

Mass analysis (M+): 438.

Elemental Analysis: Calculated for $C_{24}H_{38}O_7$: C, 65.71%; H, 8.74%. Found: C, 65.82%; H, 8.68%.

Infrared Absorption Spectrum (KBr) $\nu_{max}$ cm$^{-1}$: 3450, 1720, 1260.

Nuclear Magnetic Resonance Spectrum (CDCl$_3$) δ ppm: 3.9 (2H, multiplet); 4.3 (1H, multiplet) 4.7 (1H, multiplet); 5.3 (1H, multiplet); 5.9 (1H, doublet).

EXAMPLE 17

Sodium 3',5'-dihydroxy-(DH.MB-530B-carboxylate)

To a suspension of 438 mg of the lactone prepared in Example 16 in 20 ml of a 1:1 by volume mixture of acetone and water was added dropwise 1 ml of a 1 N aqueous solution of sodium hydroxide, whilst maintaining the pH at a value no greater than 12, over a period of 2 hours. The reaction mixture was then adjusted to a pH of 8.5 by the addition of a small quantity of 0.1 N hydrochloric acid. The acetone was distilled off under reduced pressure and the residue was freeze-dried to give 480 mg of the desired product as a hygroscopic powder.

Mass analysis (M+): 478.

Elemental Analysis: Calculated for $C_{24}H_{39}O_8Na$: C, 60.21%; H, 8.22%. Found: C, 60.43%; H, 8.19%.

Infrared Absorption Spectrum (KBr) $\nu_{max}$ cm$^{-1}$: 3300, 1730, 1710, 1580.

Nuclear Magnetic Resonance Spectrum (D$_2$O): 2.8 (2H, multiplet); 4.5 (3H, multiplet); 5.7 (1H, multiplet); 6.4 (1H, doublet).

EXAMPLE 18

Methyl 3',5'-dihydroxy-(DH.MB-530B-carboxylate)

To a solution of 480 mg of the sodium salt prepared as described in Example 17 in 3 ml of dimethylformamide were added 50 mg of potassium carbonate and 150 mg of methyl iodide, and the mixture was allowed to react at room temperature for 4 hours. Water was then added to the reaction mixture, which was then extracted with ethyl acetate. The extract was concentrated by evaporation under reduced pressure to give an oily substance, which, on purification through a Lobar column (RP-8, eluted with a 55:45 by volume mixture of methanol and water), afforded 400 mg of the desired product as an oily substance.

Mass analysis (M+): 470.

Elemental Analysis: Calculated for $C_{25}H_{42}O_8$: C, 63.78%; H, 9.00%. Found: C, 63.85%; H, 9.12%.

Infrared Absorption Spectrum (liquid film) $\nu_{max}$ cm$^{-1}$: 3400, 1730.

Nuclear Magnetic Resonance Spectrum (CDCl$_3$) δ ppm: 2.4 (2H, multiplet); 3.7 (3H, singlet); 5.3 (1H, multiplet); 5.9 (1H, multiplet).

EXAMPLE 19

MB-530B 4'a,5'-Epoxide

To a solution of 400 mg of MB-530B in 40 ml of ethyl acetate were added 320 mg of m-chloroperbenzoic acid and the resulting mixture was reacted at room temperature for 1 hour. It was then washed with 40 ml of a 5% w/v aqueous solution of sodium sulphite and 40 ml of a saturated aqueous solution of sodium chloride, after which it was dried over anhydrous sodium sulphate and then the solvent was distilled off under reduced pressure to give 390 mg of the desired product.

Mass analysis (M+): 418.

Elemental Analysis: Calculated for $C_{23}H_{34}O_6$: C, 66.03%; H, 8.13%. Found: C, 66.21%; H, 8.31%.

Infrared Absorption Spectrum (KBr) $\nu_{max}$ cm$^{-1}$: 3450, 1720.

Nuclear Magnetic Resonance Spectrum (CDCl$_3$) δ ppm: 2.7 (2H, doublet); 3.0 (1H, singlet); 4.3 (1H, multiplet); 4.7 (1H, multiplet); 5.1 (1H, multiplet); 5.2 (1H, quartet); 6.25 (1H, quartet).

We claim:

1. Compounds of formula (Id):

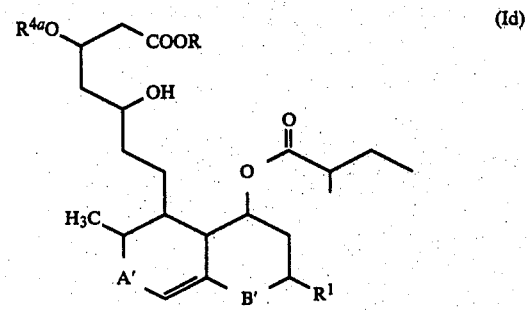

wherein:

R represents an alkali metal or a straight or branched chain $C_1$-$C_4$ alkyl group;

$R^1$ represents a hydrogen atom or a methyl group;

$R^{4a}$ represents a hydrogen atom or a straight or branched chain $C_1$-$C_6$ alkanoyl group;

A' represents a group of formula

in which $R^8$ represents a hydrogen atom, a straight or branched chain $C_1$-$C_4$ alkyl group or a straight or branched chain $C_2$-$C_6$ alkanoyl group, a group of formula

in which X represents a halogen atom, or a group of formula

and

B' represents a group of formula

in which $R^9$ represents a hydrogen atom or a straight or branched chain $C_2$-$C_6$ alkanoyl group, a group of formula

in which X is as defined above, or a group of formula

2. Methyl 3',5'-dihydroxy-(DH.ML-236B-carboxylate) of the formula of claim 1.

3. Sodium 3',5'-dihydroxy-(DH.ML-236B-carboxylate) of the formula of claim 1.

4. Methyl 3'-bromo-5'-acetoxy-(DH.ML-236B-carboxylate) of the formula of claim 1.

5. Methyl 3'-acetoxyl-5'-bromo-(DH.ML-236B-carboxylate) of the formula of claim 1.

6. Methyl 3'-methoxy-5'-hydroxy-(DH.ML-236B-carboxylate) of the formula of claim 1.

* * * * *

UNITED STATES PATENT AND TRADEMARK OFFICE
CERTIFICATE OF CORRECTION

PATENT NO. : 4,438,277

DATED : March 20, 1984

INVENTOR(S) : Akira TERAHARA et al

It is certified that error appears in the above-identified patent and that said Letters Patent is hereby corrected as shown below:

Title page, right column, 6th line from bottom, after "bond" insert -- ---- --.

Column 10, line 23, after "$-\overset{\underset{\|}{O}}{C}-$," insert --and--.

Column 19, line 28: replace "TM" with --TH--.

Column 19, line 58: after "3',5'-" insert -- dihydroxy- --.

Column 53, lines 15 and 37: replace "$\nu_{max}$" with --$\lambda_{max}$--.

Signed and Sealed this

Thirtieth Day of July 1985

[SEAL]

Attest:

DONALD J. QUIGG

*Attesting Officer*   *Acting Commissioner of Patents and Trademarks*